(12) United States Patent
Goto

(10) Patent No.: US 9,750,473 B2
(45) Date of Patent: Sep. 5, 2017

(54) THREE-DIMENSIONAL IMAGE CONSTRUCTION APPARATUS AND THREE-DIMENSIONAL IMAGE CONSTRUCTION METHOD

(71) Applicant: HITACHI, LTD., Tokyo (JP)

(72) Inventor: Yoshihiro Goto, Tokyo (JP)

(73) Assignee: HITACHI, LTD., Tokyo (JP)

( * ) Notice: Subject to any disclaimer, the term of this patent is extended or adjusted under 35 U.S.C. 154(b) by 233 days.

(21) Appl. No.: 14/413,789

(22) PCT Filed: Jul. 30, 2013

(86) PCT No.: PCT/JP2013/070572
§ 371 (c)(1),
(2) Date: Jan. 9, 2015

(87) PCT Pub. No.: WO2014/021301
PCT Pub. Date: Feb. 6, 2014

(65) Prior Publication Data
US 2015/0138187 A1    May 21, 2015

(30) Foreign Application Priority Data
Aug. 2, 2012  (JP) .................... 2012-171810

(51) Int. Cl.
*A61B 6/00*   (2006.01)
*G06T 15/00*  (2011.01)
*G06T 19/00*  (2011.01)

(52) U.S. Cl.
CPC .............. *A61B 6/466* (2013.01); *G06T 15/00* (2013.01); *G06T 19/00* (2013.01);
(Continued)

(58) Field of Classification Search
None
See application file for complete search history.

(56) References Cited

U.S. PATENT DOCUMENTS

2009/0016483 A1* 1/2009 Kawasaki .......... A61B 5/02007
                                                   378/4
2009/0079738 A1* 3/2009 Liao .................... G06T 19/00
                                                   345/427
(Continued)

FOREIGN PATENT DOCUMENTS

JP    2001-145631 A   5/2001
JP    2005-157664 A   6/2005
(Continued)

OTHER PUBLICATIONS

"Roipoly." Image Processing Toolbox. Matlab, Jan. 23, 2004. Web. Jan. 26, 2017.*

*Primary Examiner* — Chan Park
*Assistant Examiner* — Geoffrey E Summers

(57) ABSTRACT

A calculation unit generates a depth image corresponding to a first three-dimensional image with respect to a region of interest and sets a first image region based on a depth gradient of the depth image. The calculation unit moves the origin of a projection line to the near side or far side in the projection line direction by an amount of movement B for a pixel in the first image region, constructs a depth image based on the moved origin of the projection line in the first image region, sets a second image region based on the depth gradient of the depth image based on the moved origin of the projection line in the first image region, sets the second image region as the first image region, and repeats these processes. Once end conditions are satisfied, the calculation unit constructs a second three-dimensional image based on the moved origin of the projection line.

12 Claims, 23 Drawing Sheets

(52) U.S. Cl.
CPC ............... *G06T 2207/10072* (2013.01); *G06T 2207/30004* (2013.01); *G06T 2219/008* (2013.01)

(56) References Cited

U.S. PATENT DOCUMENTS

| | | | |
|---|---|---|---|
| 2010/0284597 A1* | 11/2010 | Lee .................. | G06T 15/08 382/131 |
| 2011/0026795 A1* | 2/2011 | Leber ................ | A61B 6/037 382/131 |
| 2013/0033571 A1* | 2/2013 | Steen ................ | G06T 19/20 348/46 |

FOREIGN PATENT DOCUMENTS

| | | |
|---|---|---|
| JP | 2007-175271 A | 7/2007 |
| JP | 2008-83973 A | 4/2008 |

\* cited by examiner

FIG.11
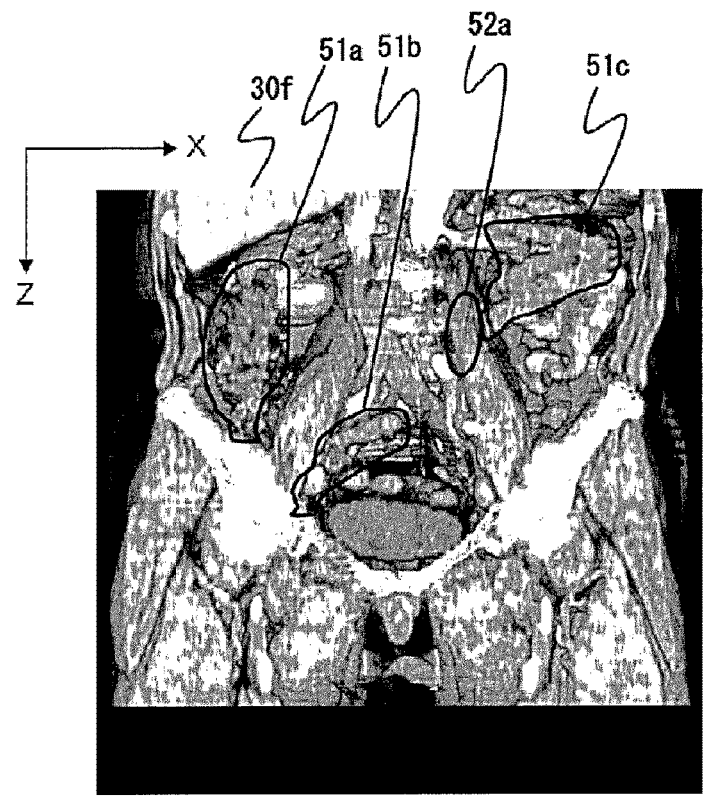
(a)
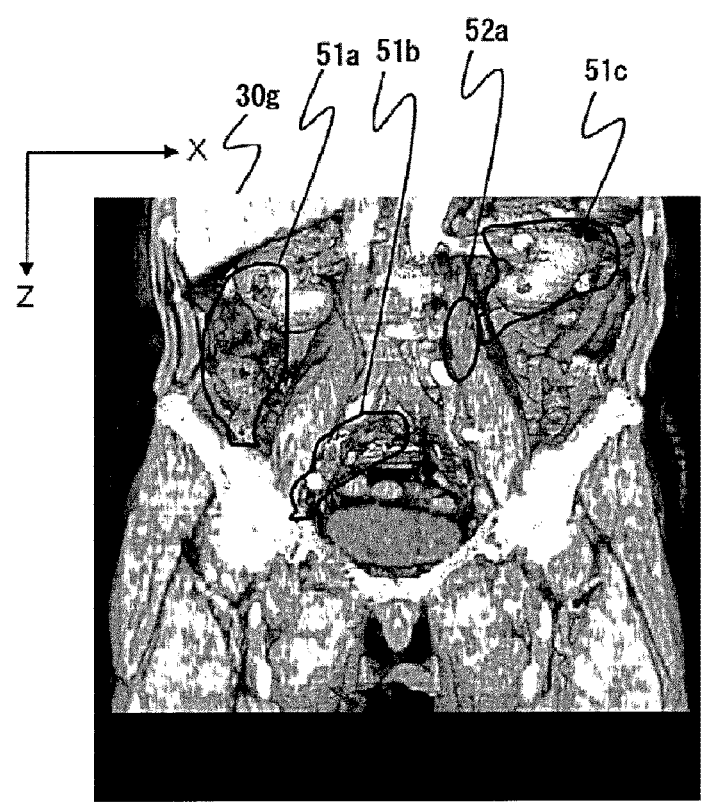
(b)

FIG.22
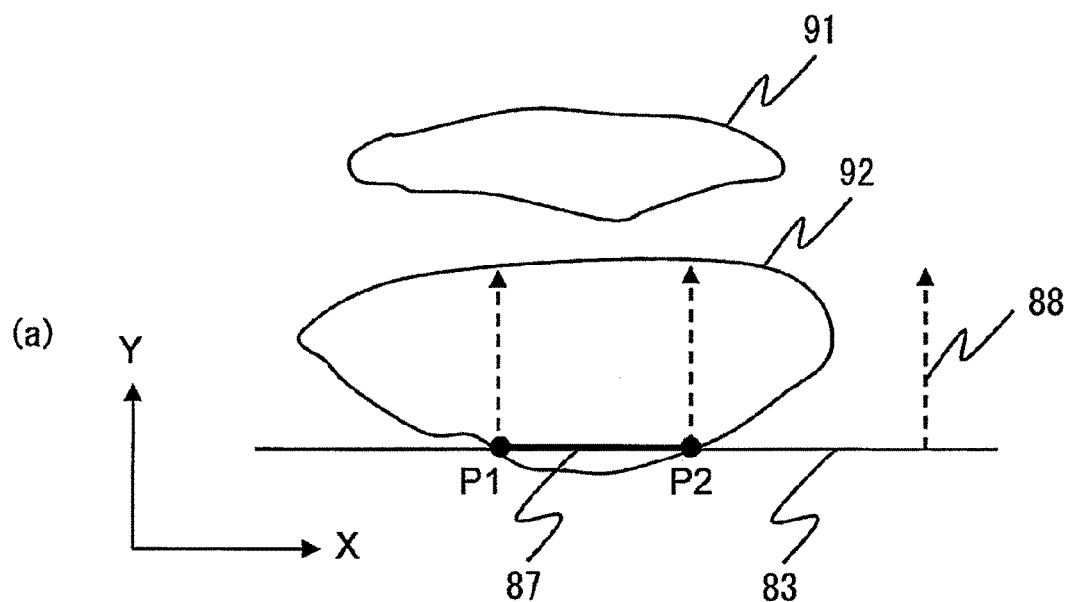
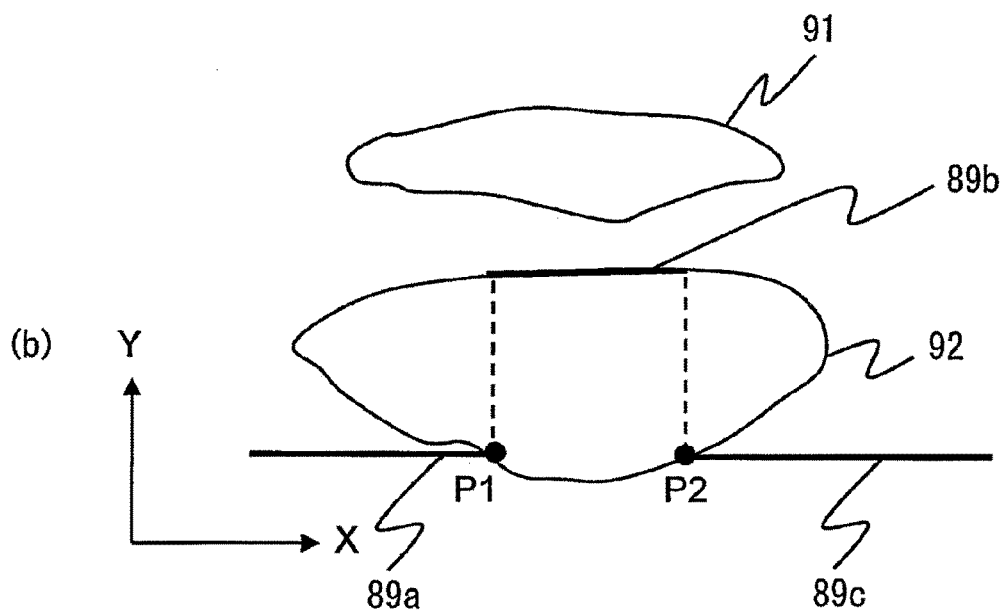

FIG.23
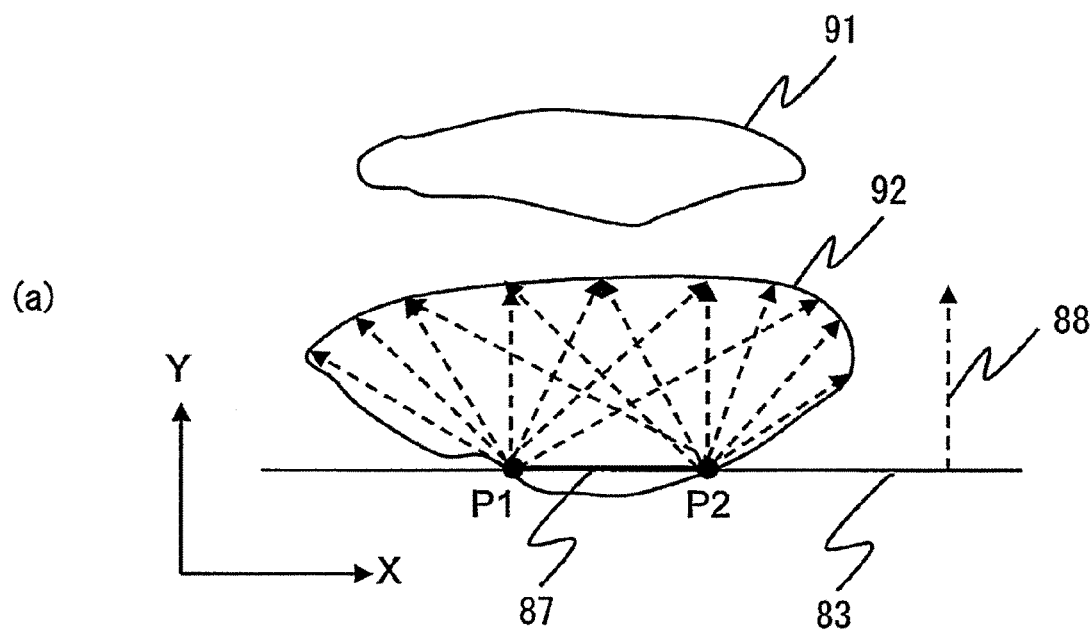
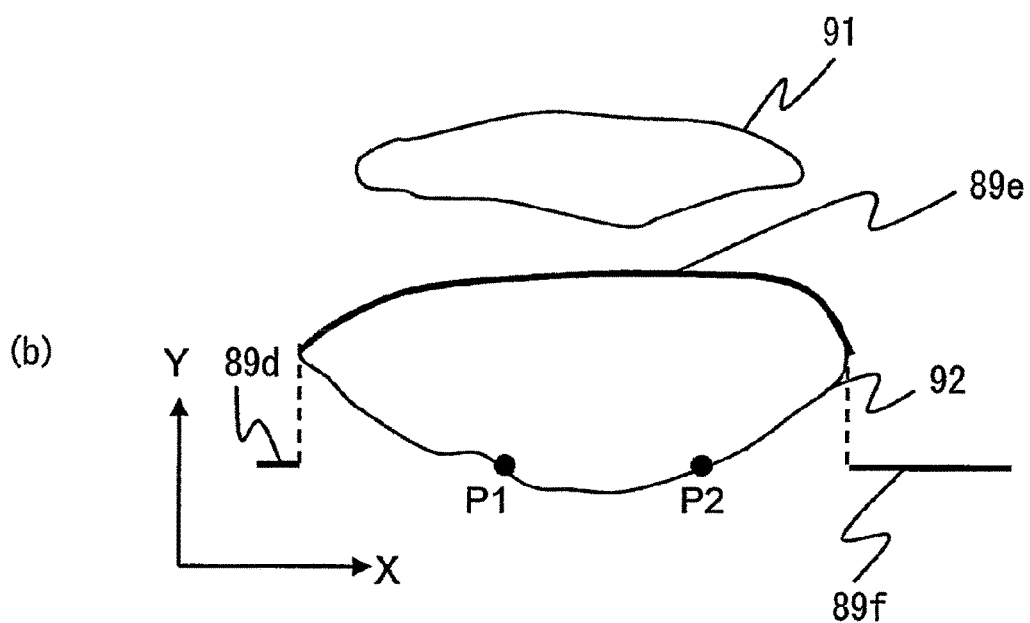

THREE-DIMENSIONAL IMAGE CONSTRUCTION APPARATUS AND THREE-DIMENSIONAL IMAGE CONSTRUCTION METHOD

TECHNICAL FIELD

The present invention relates to a three-dimensional image construction apparatus etc. that display a three-dimensional image such as a medical image.

BACKGROUND ART

Conventionally, in order to evaluate pathological changes of the urinary tract such as the renal pelvis, ureter, and urinary bladder, an excretory urography examination had been performed using X-ray imaging. However, because the information content of CT (Computer Tomography) scanning is greater than that of X-ray imaging, CT scanning examinations have been increasingly performed these days.

CT Urography is a method to evaluate pathological changes of the urinary tract using CT scanning (see Non-patent Literature 1). As described in Non-patent Literature 1, in CT Urography, scanning is performed immediately after a contrast medium is administered, and then, additionally, scanning is performed again after the contrast medium is excreted into the urinary tract. Therefore, it takes a longer time to scan than normal CT scanning. Thus, a contrast medium is administered, and it takes a longer time to scan, which results in a great burden for an object.

There is a request that urinary tract extraction is performed for data scanned without a contrast medium by image processing to display a three-dimensional image of the urinary tract. Region growing processing (Region Growing) is well known as organ extraction processing to display certain organs three-dimensionally (see Patent Literature 1). The method described in PTL 1 has achieved highly reliable region extraction by combining and using a condition in light of a local concentration change and a condition in light of a global concentration change as a growing condition in region growing processing.

CITATION LIST

Patent Literature

Patent Literature 1: Japanese Patent No. 2845995

Non-Patent Literature

Non-patent Literature 1: http://kompas.hosp.keio.ac.jp/contents/000416.html (retrieved Apr. 16, 2012) ("Keio Hospital Information & Patient Assistance Service" Article created: Feb. 2, 2009; Last updated: Dec. 28, 2011)

SUMMARY OF INVENTION

Technical Problem

However, because a CT value of the urinary tract is approximate to CT values of the surrounding organs in data scanned without a contrast medium, it is difficult to perform accurate extraction by region growing processing. For example, once only one pixel of the surrounding organs is misjudged as the urinary tract by region growing processing, the region of the urinary tract is expanded to the entire surrounding organs.

The present invention was made in light of the above-mentioned problems, and the purpose is to provide a three-dimensional image construction apparatus etc. constructing a three-dimensional image in which a certain region can be observed easily.

Solution to Problem

The first invention to achieve the above-mentioned purpose is a three-dimensional image construction apparatus comprising a display unit displaying a first three-dimensional image on a predetermined origin surface, an input unit receiving an input of a region of interest for a second three-dimensional image in the first three-dimensional image, and a calculation unit setting the origin surface as an initial value of the origin of a projection line to construct the second three-dimensional image, correcting the origin of the projection line for a pixel in the region of interest based on a depth image corresponding to the first three-dimensional image, and then constructing the second three-dimensional image using the corrected origin of the projection line for the region of the interest.

The second invention is a three-dimensional image construction method executing a step in which a display unit displays a first three-dimensional image on a predetermined origin surface, a step in which an input unit receives an input of a region of interest for a second three-dimensional image in the first three-dimensional image, a step in which a calculation unit sets the origin surface as an initial value of the origin of a projection line to construct a second three-dimensional image, a step in which a calculation unit corrects the origin of the projection line for a pixel in the region of interest based on a depth image corresponding to the first three-dimensional image, and a step in which a calculation unit constructs the second three-dimensional image using the corrected origin of the projection line for the region of interest.

Advantageous Effects of Invention

The present invention can provide a three-dimensional image construction apparatus etc. constructing a three-dimensional image in which a certain region can be observed easily.

BRIEF DESCRIPTION OF DRAWINGS

FIG. 11 is an example of a processing result.

FIG. 22 is a diagram explaining a process of constructing a three-dimensional image in the third embodiment.

FIG. 23 is a diagram explaining a process of constructing a three-dimensional image in the third embodiment.

DESCRIPTION OF EMBODIMENTS

The present invention provides a three-dimensional image construction apparatus etc. constructing a three-dimensional image in which a certain region can be observed easily. Particularly, in order to easily observe a thin target organ with a pixel value approximate to pixel values of the surrounding organs for volume data scanned without a contrast medium, the present invention provides a three-dimensional image construction apparatus etc. that can extract and delete the surrounding organs between a point of view and a target organ based on a region of interest specified by an operator and can extract and add a target organ located nearer the point of view. Hereinafter, embodiments of the present invention will be described in detail based on the diagrams.

Figure 1:
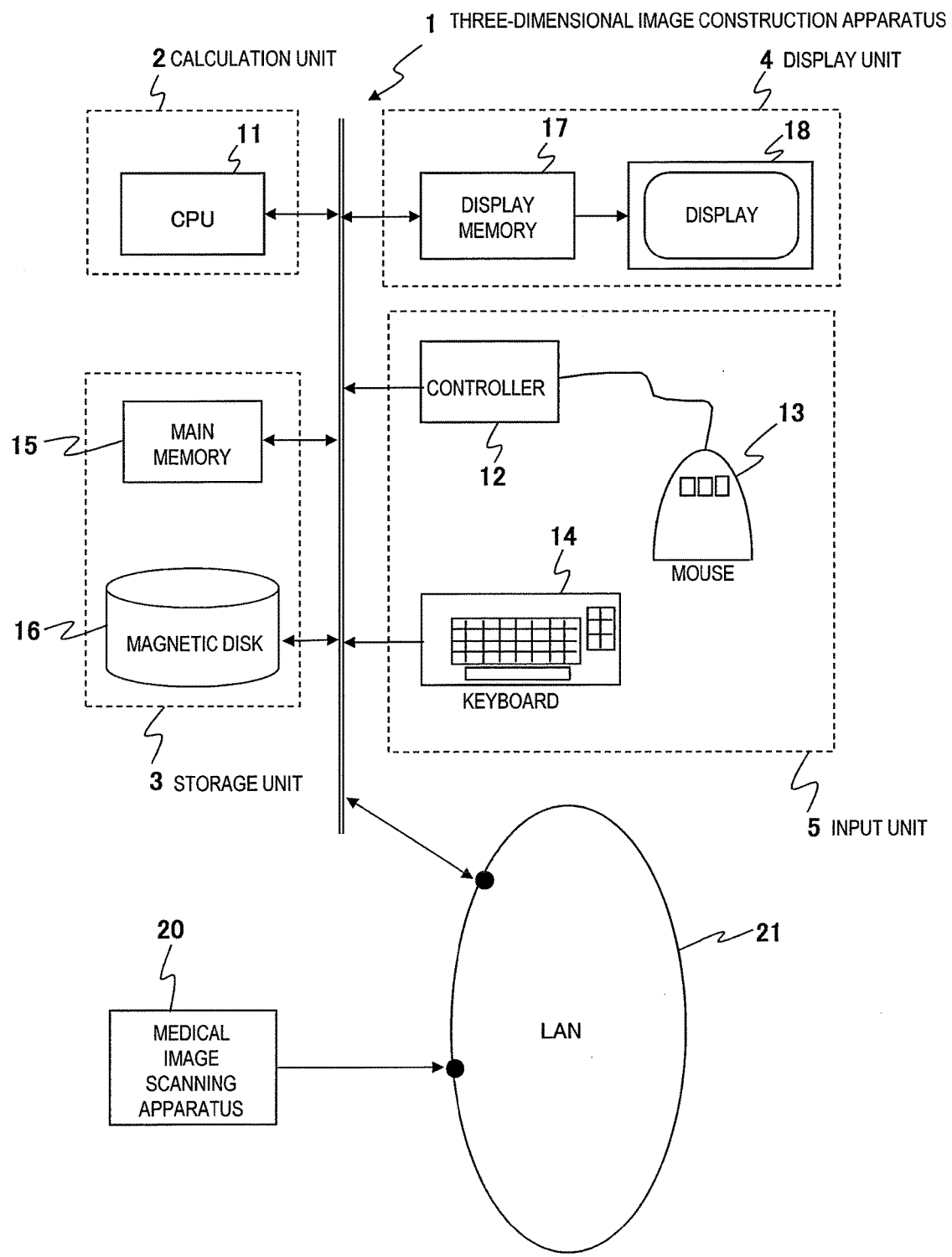
FIG. 1 is a diagram showing hardware configuration of a three-dimensional image construction apparatus.

First, hardware configuration of a three-dimensional image construction apparatus common to all the embodiments will be described. As shown in FIG. 1, the three-dimensional image construction apparatus 1 is comprised of the calculation unit 2, the storage unit 3, the display unit 4, the input unit 5, etc.

The calculation unit 2 is comprised of the CPU 11. The storage unit 3 is comprised of the main memory 15, the magnetic disk 16, etc. the display unit 4 is comprised of the display memory 17, the display 18, etc. The input unit 5 is comprised of the controller 12, the mouse 13, the keyboard 14, etc.

Each of the controller 12, the keyboard 14, the main memory 15, the magnetic disk 16, and the display memory 17 is connected to the CPU 11 via the data transfer bus 19 in a manner where signals can be transmitted and received.

The CPU 11 is also connected to the medical image scanning apparatus 20 via the data transfer bus 19 and the local area network (LAN) 21 in a manner where signals can be transmitted and received. The mouse 13 is connected to the controller 12 in a manner where signals can be transmitted and received. The display 18 is connected to the display memory 17 in a manner where signals can be transmitted and received. The phrase "in a manner where signals can be transmitted and received" shows a state where signals can be transmitted and received mutually or from one end to the other end regardless of electrically or optically wired connection and electrically or optically wireless connection.

The CPU 11 executes a computer program and controls each element to be connected. A computer program is a command for the CPU 11 combined so that an execution result of a process to be described later can be obtained.

The controller 12 communicates various data such as displacement data of a position obtained by a sensor installed in the mouse 13 and input data of a button switch installed in the mouse 13 to the CPU 11 via the data transfer bus 19. The mouse 13 supports data input by an operator. An operator moves the cursor of the mouse 13 to an image displayed on the display 18 and switches such as a radio switch etc. created by software and clicks the position of the moved cursor to communicate a predetermined input data to the CPU 11. The keyboard 14 is an input device in a case where character input is mainly suitable, such as ID information to identify a medical image that an operator wants to retrieve from the magnetic disk 16 and a diagnostic report of a medical image to be displayed on the display 18.

The main memory 15 is used as a work area of the CPU 11 in a case such as where the main memory 15 loads various computer programs from the magnetic disk 16 and where the main memory 15 memorizes medical image data and progress of calculation when the CPU 11 executes various computer programs. The magnetic disk 16 memorizes various computer programs. Also, the magnetic disk 16 receives and memorizes scan data of an object scanned by the medical image scanning apparatus 20 via the LAN 21 and the data transfer bus 19. The magnetic disk 16 is an example of external storage devices in a computer system. The external storage devices include various storage media such as a flexible disk, an optical (magnetic) disk, a ZIP memory, and a USB memory.

The display memory 17 temporarily memorizes data to be displayed on a screen from among calculation results of the CPU 11 before a signal is transferred to the display 18. The display 18 displays a medical image transferred by signal from the display memory 17 and various information accompanied by the medical image.

The data transfer bus 19 transfers data between each element to be connected to the data transfer bus 19. The medical image scanning apparatus 20 is an apparatus such as an X-ray CT apparatus, an MRI apparatus, an ultrasound apparatus, a scintillation camera apparatus, a PET apparatus, and a SPECT apparatus that can obtain a tomographic image of an object. The LAN 21 connects the medical image scanning apparatus 20 and the three-dimensional image construction apparatus 1 in a manner where signals can be transmitted and received. Also, public lines such as the Internet may be used instead of the LAN 21.

Although the display 18 comprising the display unit 4 as well as the mouse 13 and the keyboard 14 comprising the input unit 5 are separated in the previous description, the display unit 4 and the input unit 5 may be an integrated device such as a touch panel display.

First Embodiment

Referring to FIGS. 2 to 17, the first embodiment will be described. Hereinafter, an example will be described where a three-dimensional image to observe the kidney and the urinary tract easily is constructed for data scanned without a contrast medium. Particularly, a case where the original volume data is scanned by an X-ray CT apparatus will be described as an example.

A method to project from a point of view to a projection surface considers a point of view as a surface, and the parallel projection method that projects using a projection line parallel from the surface to a projection surface is used. Hereinafter, a surface being the origin of a projection line is referred to as "origin surface".

A three-dimensional image may be an image constructed by a surface rendering method, an image constructed by a volume rendering method, or an image (hereinafter, referred to as "depth image") constructed by a depth method. The depth method is a method that shades an image according to a distance from each pixel on a CT image to a point where it is projected, and normally, the longer the distance is, the denser (darker) the shade will be. Each pixel value of the depth image shown below is set as a distance from the origin surface to a certain pixel that satisfies a threshold value condition.

Also, hereinafter, a three-dimensional image that is used for pre-processing to construct a target image (=an image where the kidney and the urinary tract are observed easily) is referred to as "first three-dimensional image", and the target image is referred to as "second three-dimensional image".

Figure 2:
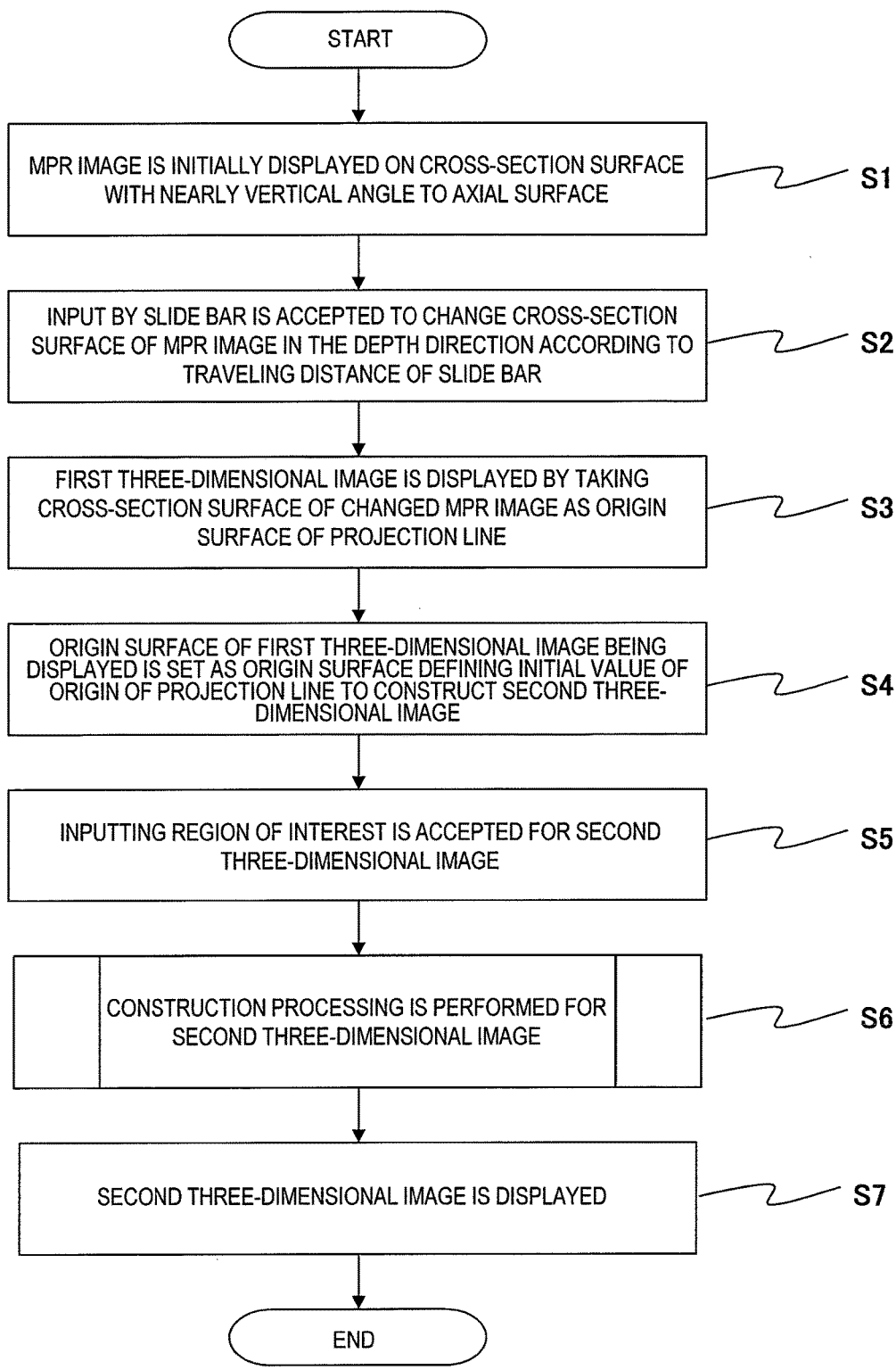
FIG. 2 is a flow chart showing the entire process flow in the first embodiment.

As shown in FIG. 2, the display unit 4 initially displays an MPR (Multi Planer Reconstruction) image in a cross section with an almost perpendicular angle to the axial surface of an object according to control by the calculation unit 2 (S1).

FIG. 4(a) shows a state where the MPR (Multi Planer Reconstruction) image 30a perpendicular to the axial surface is displayed on the display 18. In the MPR image 30a, the cross sections of the kidney 41 and the kidney 42 can be observed.

With the MPR image 30a, the display unit 4 displays the slide bar 31, the trace button 32, the two-point specifying button 33, the curve specifying button 34, and the end button 35 on the display 18. The slide bar 31 is a bar that an operator uses to specify a cross section of a first three-dimensional image to be displayed on the display 18. The trace button 32, the two-point specifying button 33, and the curve specifying button 34 are buttons that an operator uses to input a region of interest (ROIw). The detailed processes of the calculation unit 2 after the respective buttons are pressed down will be described later. The end button 35 is a button that an operator uses to provide a command to end a process.

In the above-mentioned description, one certain organ is the urinary tract, and it extends along the body-axis direction of an object. Therefore, an image to be displayed in S1 is specified as an MPR image in a cross section with an almost perpendicular angle to the axial surface of an object. In a case such as where a certain organ is not the urinary tract, an image to be displayed in S1 is not limited to this. Also, an image to be displayed in S1 is not limited to an MPR image and may be a CPR (Curved Planar Reconstruction) image.

Going back to the description of FIG. 2, next, the calculation unit 2 receives input by the slide bar 31 via the input unit 5 and changes a cross section of an MPR image toward the depth direction of the screen according to the moving distance of the slide bar 31 (S2). For example, the calculation unit 2 changes the cross section to the near side of the screen when the slide bar 31 is moved upward and changes the cross section to the far side of the screen when the slide bar 31 is moved downward. The display unit 4 displays an MPR image after the change according to control by the calculation unit 2.

FIG. 4(b) shows a state where the MPR image 30b in a cross section different from that of the MPR image 30a in FIG. 4(a) is displayed on the display 18. In the MPR image 30b, the ventral end 43 of the kidney can be observed.

Going back to the description of FIG. 2, next, the calculation unit 2 constructs a first three-dimensional image by specifying the cross section of the MPR image after the change as the origin surface of a projection line. The display unit 4 displays the first three-dimensional image to be constructed according to control by the calculation unit 2 (S3).

By specifying the cross section of the MPR image 30b of FIG. 4(b) as the origin surface of a projection line, FIG. 5(a) shows a state where the first three-dimensional image 30c constructed by projecting the projection line to the far side of the screen is displayed on the display 18. Because the ventral end 43 of the kidney can be observed in the MPR image 30b as described above, the first three-dimensional image 30c is to be constructed by projecting a projection line from the origin surface passing through the ventral end 43 of the kidney to the far side of the screen.

In the first three-dimensional image 30c, a part of the two kidneys is hidden by the surrounding organs (those on the near side of the screen) and cannot be observed. Also, in the first three-dimensional image 30c, a part of the urinary tract 44 and the urinary tract 45 cannot be observed. A part of the urinary tract 44 is hidden by the surrounding organs (those on the near side of the screen) and cannot be observed. On the other hand, a part of the urinary tract 45 is located on the nearer side of the screen than the origin surface and cannot be observed.

In the following process, in order to construct a second three-dimensional image where the kidney and the urinary tract can be observed easily, the calculation unit 2 extracts and deletes the surrounding organs between the origin and the kidney as well as the urinary tract and extracts and adds the urinary tract located nearer the origin surface based on a region of interest (ROIw) specified by an operator.

Going back to the description of FIG. 2, next, the calculation unit 2 sets the origin surface of the first three-dimensional image being displayed currently as the origin that defines an initial value of the origin of a projection line to construct a second three-dimensional image (S4). The calculation unit 2 memorizes an initial value the origin of the projection line for each projection line in the storage unit 3. Additionally, the number of projection lines is the same as the number of pixels of the projection surface.

Next, the calculation unit 2 receives input of a region of interest (ROIw) for the second three-dimensional image via the input unit 5 (S5).

FIG. 5(b) shows a state where the first three-dimensional image 30d in which the regions of interest 51a, 51b, 51c, and 52a are superimposed on the first three-dimensional image 30c of FIG. 5(a) is displayed on the display 18.

In an example shown in FIG. 5(b), after an operator pressed down the trace button 32 via the input unit 5 to draw a trace of the mouse pointer 40, the regions of interest 51a, 51b, 51c, and 52a are input.

The regions of interest 51a, 51b, and 51c are regions to extract and delete the surrounding organs between the origin and the kidney as well as the urinary tract. In the regions of interest 51a, 51b, and 51c, for example, a trace of the mouse pointer 40 is drawn while left-clicking the mouse 13.

The region of interest 52a is a region to extract and add the urinary tract located nearer than the origin. In the region of interest 52a, for example, a trace of the mouse pointer 40 is drawn while right-clicking the mouse 13.

Figure 6:
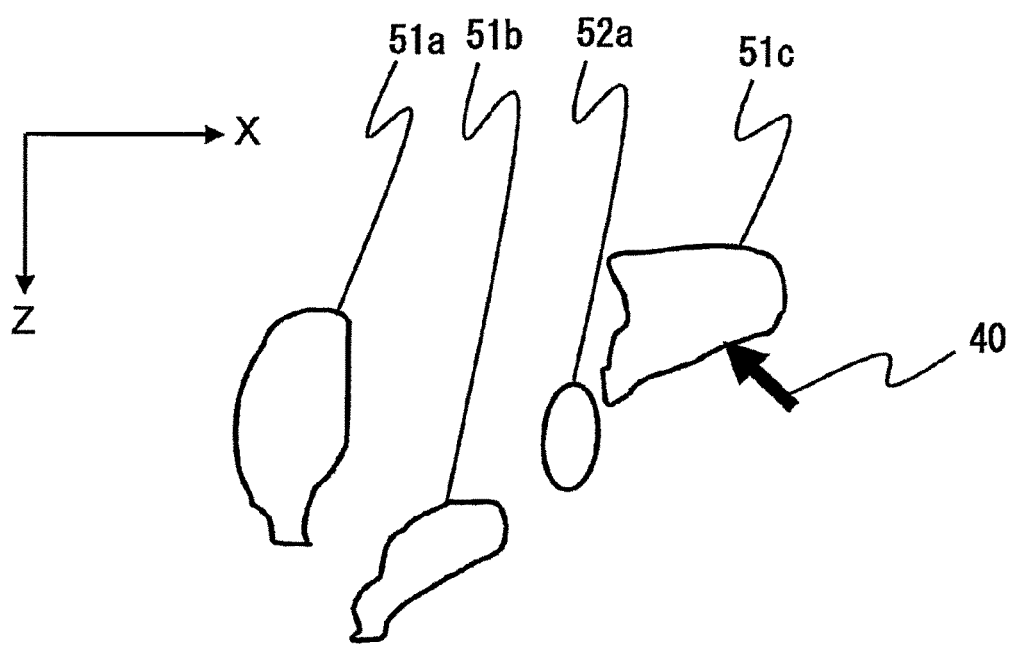
FIG. 6 is a diagram explaining an input receiving process of a region of interest.

Additionally, because FIG. 5(b) is converted into the grayscale image due to the limitations of patent drawings, it is difficult to visually recognize a trace of a region of interest. Then, FIG. 6 shows only a positional relationship between a trace of a region of interest and the mouse pointer. Actually, because the display unit 4 displays a trace of a region of interest and the mouse pointer in a color different from that of the first three-dimensional image according to the control by the calculation unit 2, an operator can visually recognize a trace of a region of interest and the mouse pointer easily.

Going back to the description of FIG. 2, next, the calculation unit 2 executes construction processing of a second three-dimensional image (S6). The details of construction processing of the second three-dimensional image are shown in FIG. 3.

Figure 3:
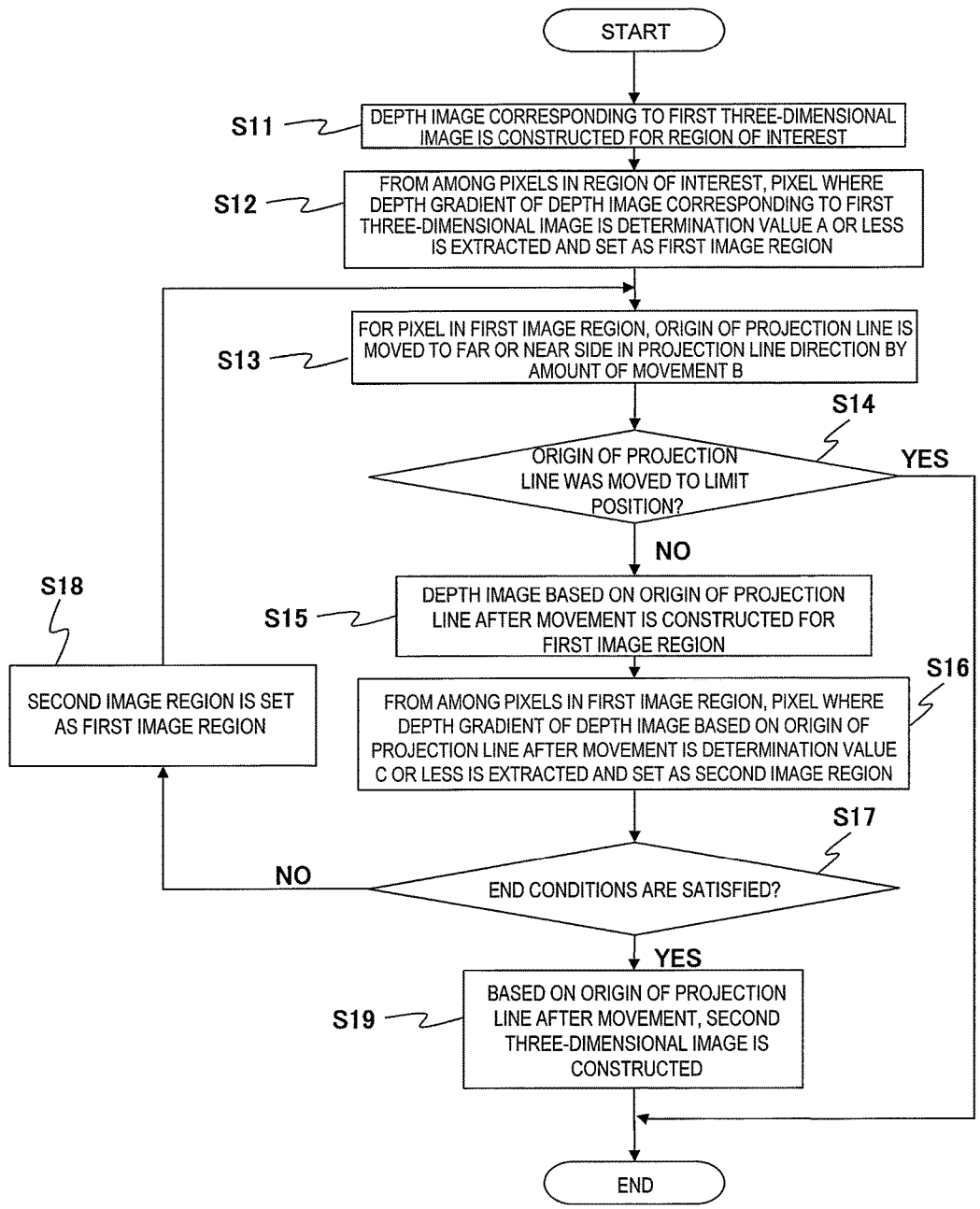
FIG. 3 is a flow chart showing a process flow of constructing a three-dimensional image.
Figure 4:
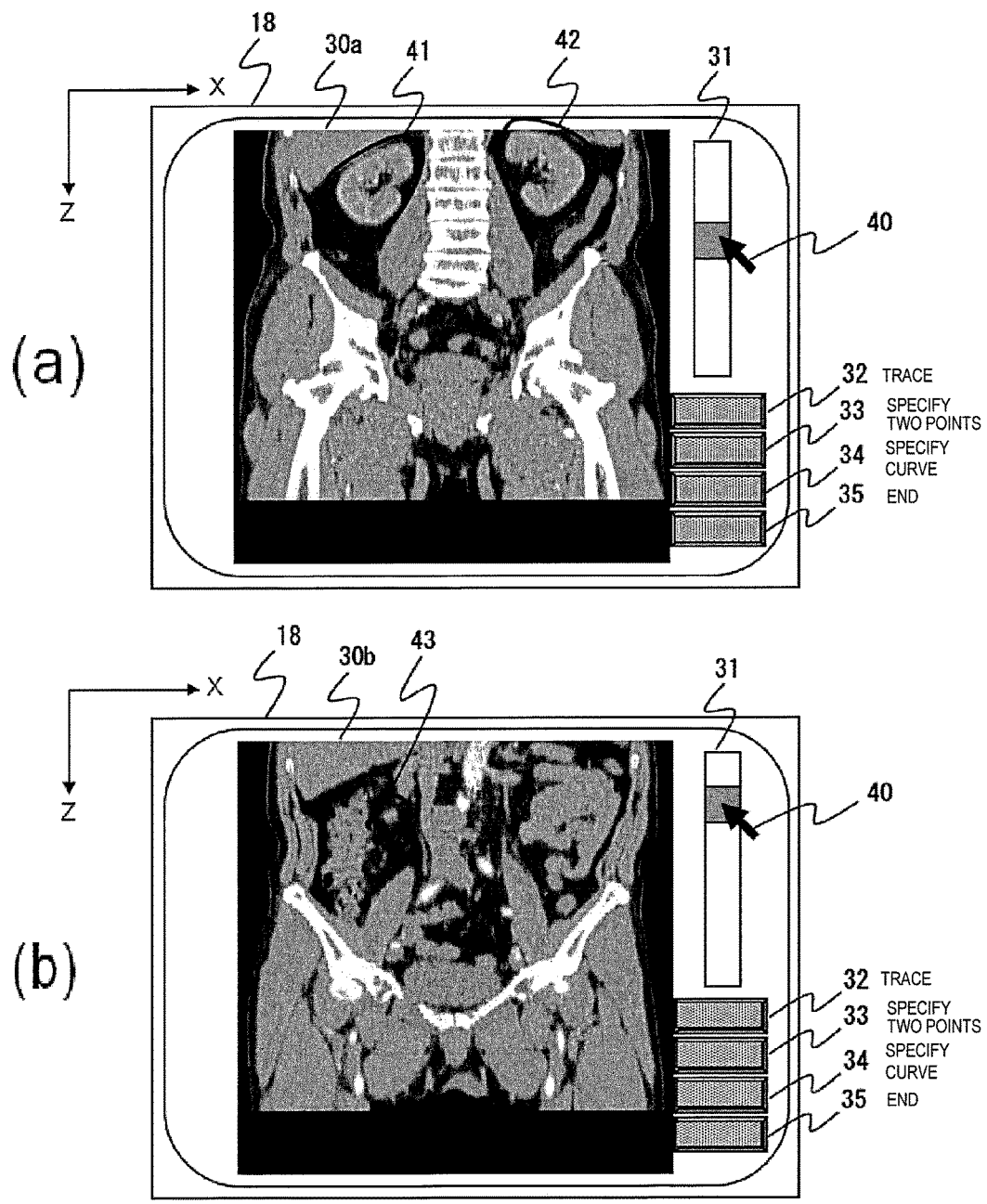
FIG. 4 is a diagram explaining a process of setting the origin surface.
Figure 5:
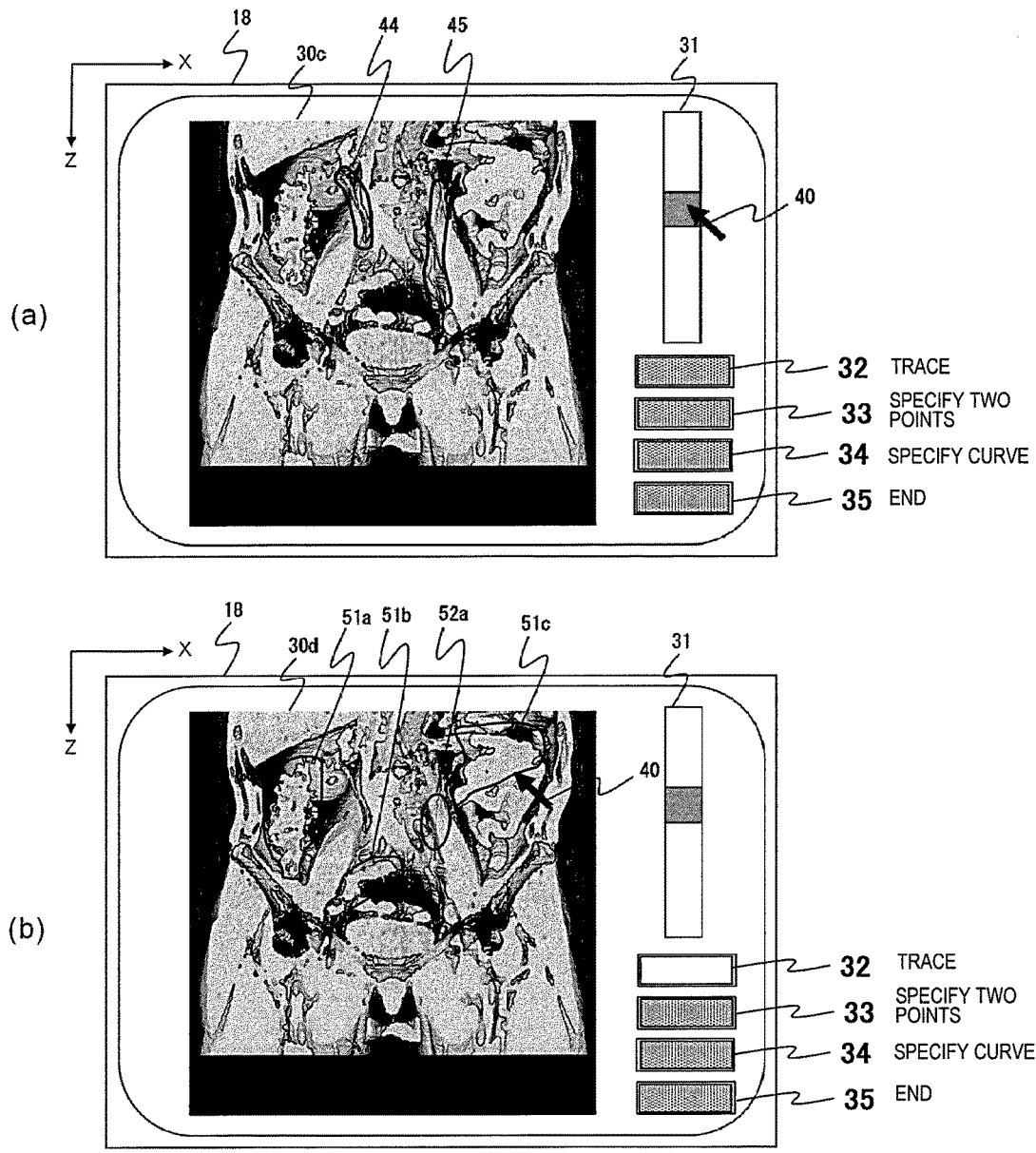
FIG. 5 is a diagram explaining an input receiving process of a region of interest.

As shown in FIG. 3, the calculation unit 2 generates a depth image corresponding to the first three-dimensional image for a region of interest received in S5 (S11). The calculation unit 2 uses the first three-dimensional image being displayed as is when the first three-dimensional image being displayed is a depth image. Also, the calculation unit 2 performs conversion processing into a depth image from the first three-dimensional image (such as a surface rendering image and a volume rendering image) by a known art when the first three-dimensional image is not a depth image.

Next, the calculation unit 2 extracts a pixel where a depth gradient of a depth image corresponding to the first three-dimensional image is the determination value A or less from among pixels in a region of interest and sets the pixel as a first image region (ROI1) (S12).

Figure 7:
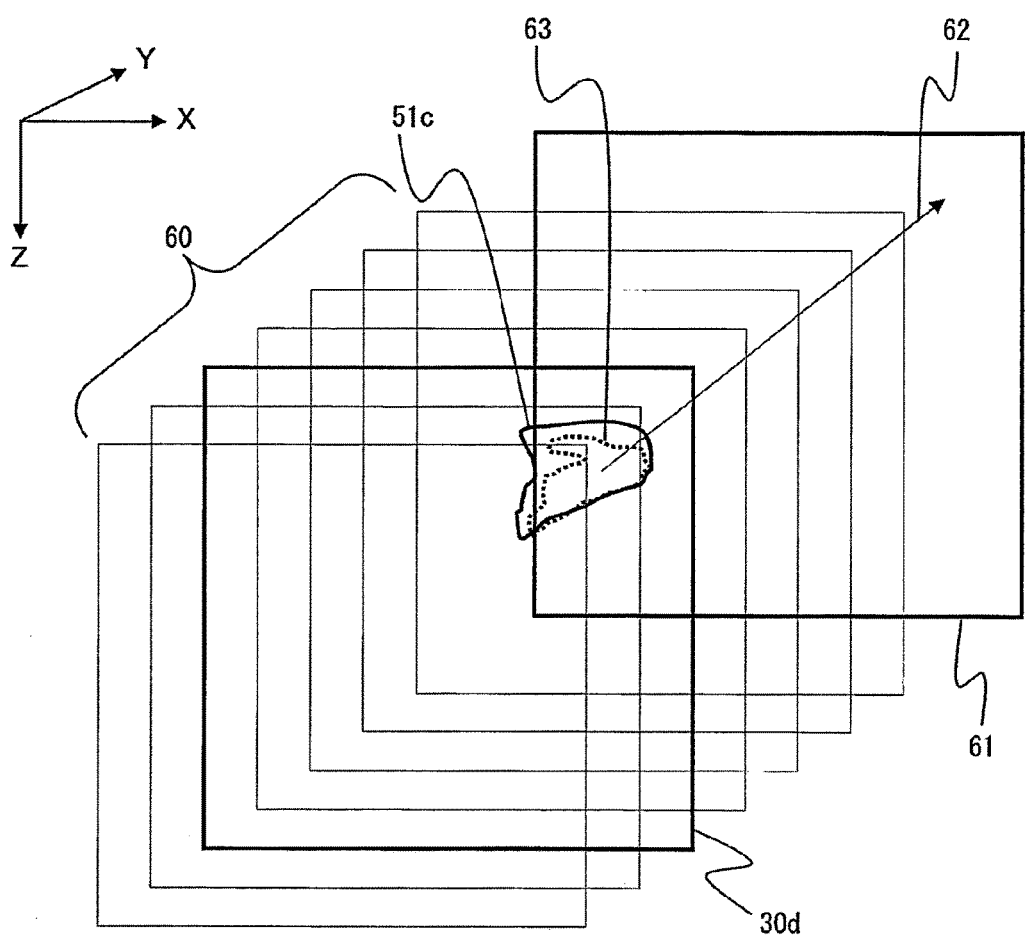
FIG. 7 is a diagram explaining a process of constructing a three-dimensional image.

FIG. 7 shows the region of interest 51c and the corresponding first image region 63 schematically.

The planar surface group 60 is entirely parallel to the XZ planar surface. The cross section of the first three-dimensional image 30d that is one of the planar surface group 60 is also parallel to the XZ planar surface. For a projection line to construct a second three-dimensional image, any of the planar surface group 60 is specified as the origin, and a point on the projection surface 61 is specified as the ending point. The region of interest 51c is located on the cross section of the first three-dimensional image 30d. The corresponding first image region 63 is also located on the cross section of the first three-dimensional image 30d as of S12. The calculation unit 2 extracts and deletes the surrounding organs between the origin and the kidney as well as the urinary tract and extracts and adds the urinary tract located nearer than the origin, which is achieved by correcting the projection line to construct the second three-dimensional image as any point of the planar surface group 60 to the near side or far side in the depth direction for a pixel in the first image region 63 in a process to be described later.

Figure 8:
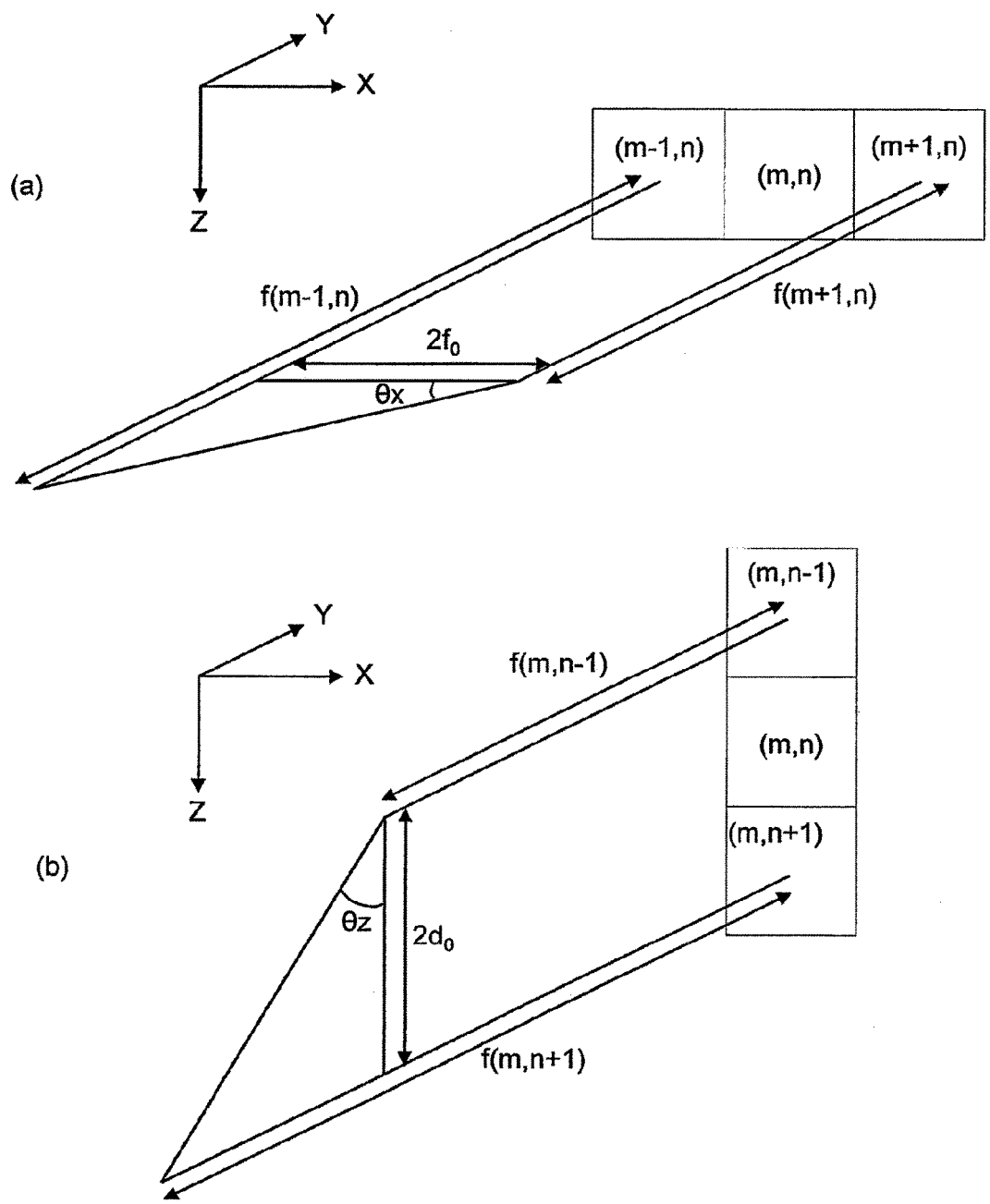
FIG. 8 is a diagram explaining a process of constructing a three-dimensional image.
Figure 9:
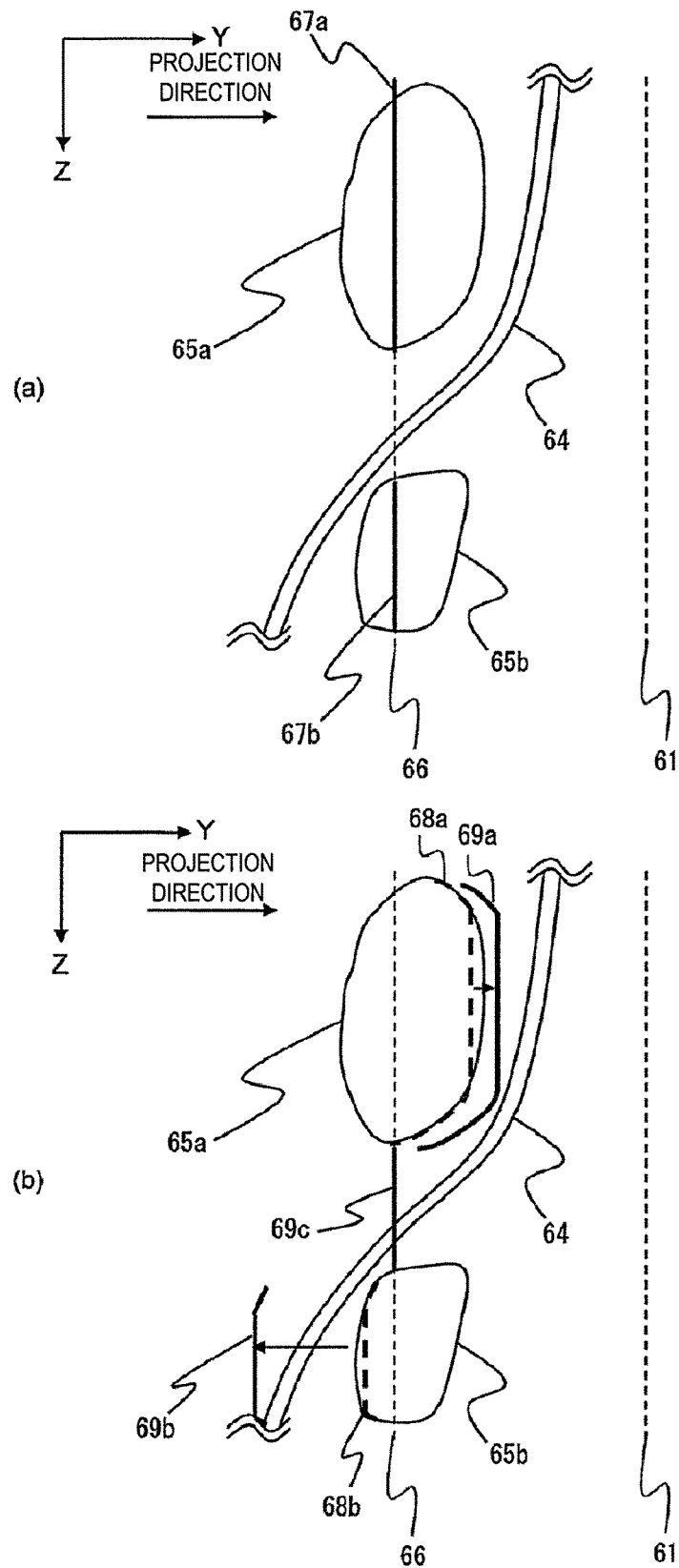
FIG. 9 is a diagram explaining a process of constructing a three-dimensional image.

FIG. 8 is a schematic diagram to describe a depth gradient of a depth image corresponding to a first three-dimensional image. The depth gradient g (m, n) of a target pixel (m, n), for example, are defined by the following formula.

[Formula 1]

$$g(m,n)=1-\cos\theta x \cdot \cos\theta z \quad (1)$$

where $$\tan\theta x = |f(m-1,n)-f(m+1,n)|/2d_0$$

$$\tan\theta z = |f(m,n-1)-f(m,n+1)|/2d_0$$

(m−1, n): a left adjacent pixel to a target pixel, (m+1, n): a right adjacent pixel to a target pixel, (m, n−1): an upper adjacent pixel to a target pixel, (m, n+1): a lower adjacent pixel to a target pixel, f(x, z): a distance from the origin surface to a pixel (x, z), and $d_0$: a distance between adjacent pixels.

FIG. 8(a) shows θx. FIG. 8(b) shows θz. Additionally, although FIG. 8 shows an example of the X-Z planar surface, calculation can also be performed for the other cross sections similarly.

A depth gradient g (m, n) calculated by the formula (1) is 0 g(m, n)<1 based on the definition. Also, in a case where a projection surface and the origin surface are parallel, a depth gradient g (m, n) becomes a value close to 0 when the vicinity of a target pixel (m, n) is a flat region, and a depth gradient g (m, n) becomes a value close to 1 when the vicinity of a target pixel (m, n) is an uneven region.

In S12 described above, a pixel that should be extracted as a first image region (ROI1) is a pixel that belongs to a flat region where the surrounding organs are separated. Therefore, it is desired that the calculation unit 2 extracts a pixel where the depth gradient is the determination value A or less as a first image region (ROI1) and that the determination value A in S12 becomes a value close to 0.

Going back to the description of FIG. 3, next, the calculation unit 2 moves the origin of the projection line to the far side or the near side in the projection line direction by the amount of movement B for a pixel in the first image region (ROI1) (S13). The calculation unit 2 updates the origin of the projection line for each pixel memorized in the storage unit 3 to a post-movement position.

Additionally, the origin of the projection line is updated only for a pixel in the first image region (ROI1).

Next, the calculation unit 2 checks whether the origin of the projection line has moved to a limit position or not (S14). The limit positions are, for example, a position where original volume data does not exist, a position that exceeds a value of "a preset limit movement amount=an amount of movement B×limit movement frequencies", etc.

In a case where the origin of the projection line has moved to a limit position (Yes for S14), the calculation unit 2 ends the process. In this case, a second three-dimensional image is not constructed.

In a case where the origin of the projection line has not moved to a limit position (No for S14), the calculation unit 2 constructs a depth image that is based on the post-movement origin of the projection line for the first image region (ROI1) (S15).

Next, the calculation unit 2 extracts a pixel where a depth gradient of a depth image based on the post-movement origin of the projection line is the determination value C or less from among pixels in the first image region (ROI1) and set the pixel as the second image region (ROI2) (S16).

Next, the calculation unit 2 checks whether end conditions are satisfied or not (S17). The area (synonymous with the number of pixels) of the first image region (ROI1) is specified as S1, and the area of the second image region (ROI2) is specified as S2. The first example of the end conditions is "100×S1/S2<Determination Value D" (however, D is a value of 100 or less). This means that a value where the area S1 of the first image region (ROI1) was divided by the area S2 of the second image region (ROI2) is less than a constant value of 1 or less.

The second example of the end conditions is "S2<Determination Value E". This means that the area of the second image region (ROI2) is less than a constant value.

According to the end conditions of the second example, for example, as shown in FIG. 9(a), the movement of the origin of the projection line ends in the position of the dotted line 68a shown in FIG. 9(b) in a case where the surrounding organ 65a is located on the near side of the particular organ 64 in the region of interest 67a. Then, in the region of interest 67a, the calculation unit 2, for example, extracts and deletes the surrounding organ 65a between the origin surface 66 and the particular organ 64, which can be achieved by specifying the solid line 69a where the dotted line 68a is slightly shifted in the projection direction as the origin of a projection line to be used for the second three-dimensional image.

Also, for example, as shown in FIG. 9(a), in a case where the particular organ 64 is located in front of the origin surface 66 in the region of interest 67b, the movement of the origin of the projection line ends in the position of the dotted line 68b shown in FIG. 9(b). Then, in the region of interest 67b, the calculation unit 2, for example, extracts and adds the particular organ 64 located in front of the origin surface 66, which can be achieved by specifying the solid line 69b where the dotted line 68b is slightly shifted in a direction opposite to the projection direction as the origin of a projection line to be used for the second three-dimensional image.

Going back to the description of FIG. 3, in S17, in a case where the end conditions are not satisfied (No for S17), the calculation unit 2 sets the second image region (ROI2) as the first image region (ROI1) (S18) and repeats the process from S13. In a case where the end conditions are satisfied (Yes for S17), the calculation unit 2 constructs the second three-dimensional image based on the post-movement origin of the projection line memorized in the storage unit 3 (S19). In order to perform the process in S19, a known three-dimensional image construction method may be used.

Because the origin is set to an appropriate position for each projection line by the above process, the calculation unit 2 can construct a desired image (=an image where the kidney and the urinary tract are observed easily).

Going back to the description of FIG. 2, the display unit 4 displays the second three-dimensional image generated in S6 according to the control by the calculation unit 2. An operator can observe the kidney and the urinary tract easily by interpreting the second three-dimensional image.

Figure 10:
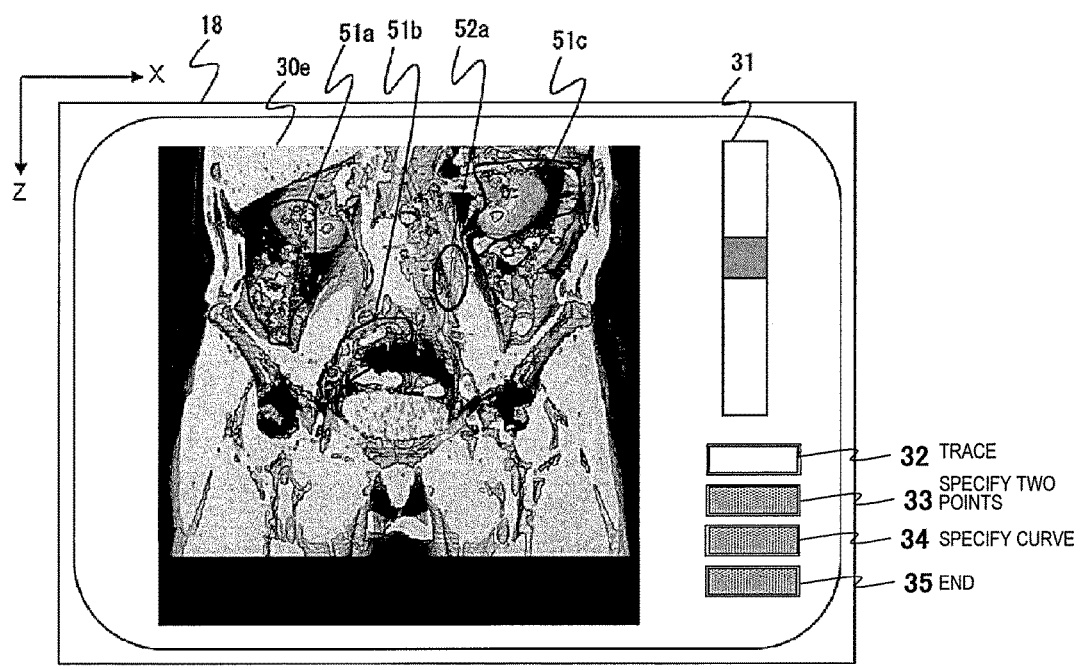
FIG. 10 is an example of a processing result.

FIG. 10 shows a state where the second three-dimensional image 30e is constructed based on the regions of interest 51a, 51b, 51c, and 52a input in the first three-dimensional image 30d in FIG. 5(b) and is displayed on the display 18.

In the region of interest 51a, most of the surrounding organs located in front of the kidney and obscuring it are deleted, which can make the kidney observation easy. Also, in the region of interest 51b, a part of the surrounding organs located in front of the urinary tract and obscuring it is deleted. Also, in the region of interest 51c, most of the surrounding organs located in front of the kidney and obscuring it are deleted, which can make the kidney observation easy. Also, in the region of interest 52a, the urinary tract located near the origin surface is added, which can make the urinary tract observation easy. In the second three-dimensional image 30e, and at least in the regions of interest 51a, 51c, and 52a, the kidney and the urinary tract can be observed easily.

FIG. 11(a) shows a state where the first three-dimensional image 30f that uses the opacity is displayed on the display 18. The regions of interest 51a, 51b, 51c, and 52a are superimposed in the similar position to the first three-dimensional image 30d on the first three-dimensional image 30f.

FIG. 11(b) shows a state where the second three-dimensional image 30g is constructed based on the regions of interest 51a, 51b, 51c, and 52a input in the first three-dimensional image 30f in FIG. 11(a) and is displayed on the display 18. The second three-dimensional image 30g also uses the opacity. In the second three-dimensional image 30g, and at least in the regions of interest 51a, 51c, and 52a, the kidney and the urinary tract can be observed easily.

Figure 12:
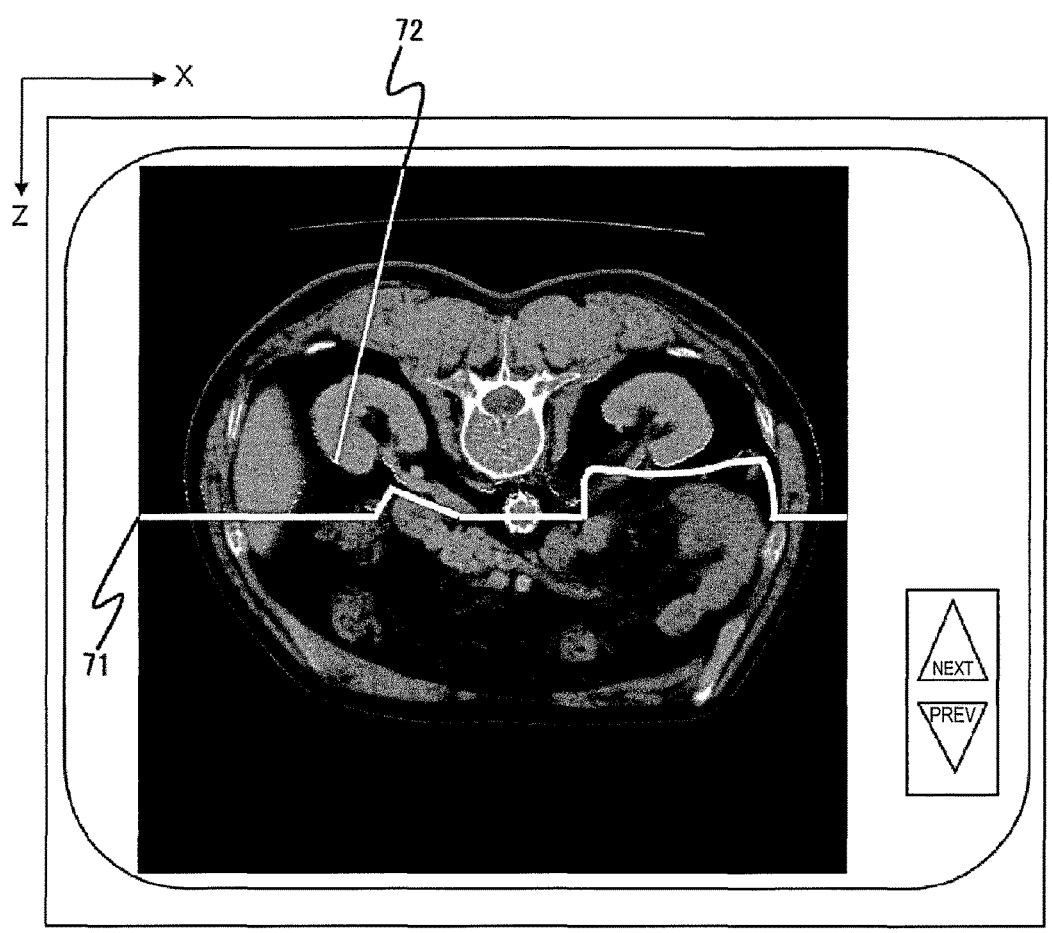
FIG. 12 is an example of a processing result.

FIG. 12 shows a state where the depth position 72 and the trace 71 of the origin of the post-correction projection line on an arbitrary axial surface are displayed on the display 18. Additionally, because FIG. 12 is converted into the grayscale image due to the limitations of patent drawings, it is difficult to visually recognize the depth position 72 and the trace 71 of the origin of the post-correction projection line. Therefore, in FIG. 12, at least, in order to visually recognize the trace 71 of the origin of the post-correction projection line easily, the trace 71 of the origin of the post-correction projection line is shown with a white thick line. Actually, because a depth position and a trace of the origin of a post-correction projection line are displayed in a color different from that of a second three-dimensional image, an operator can visually recognize the depth position and the trace of the origin of the post-correction projection line easily.

<First Variation>

Figure 13:
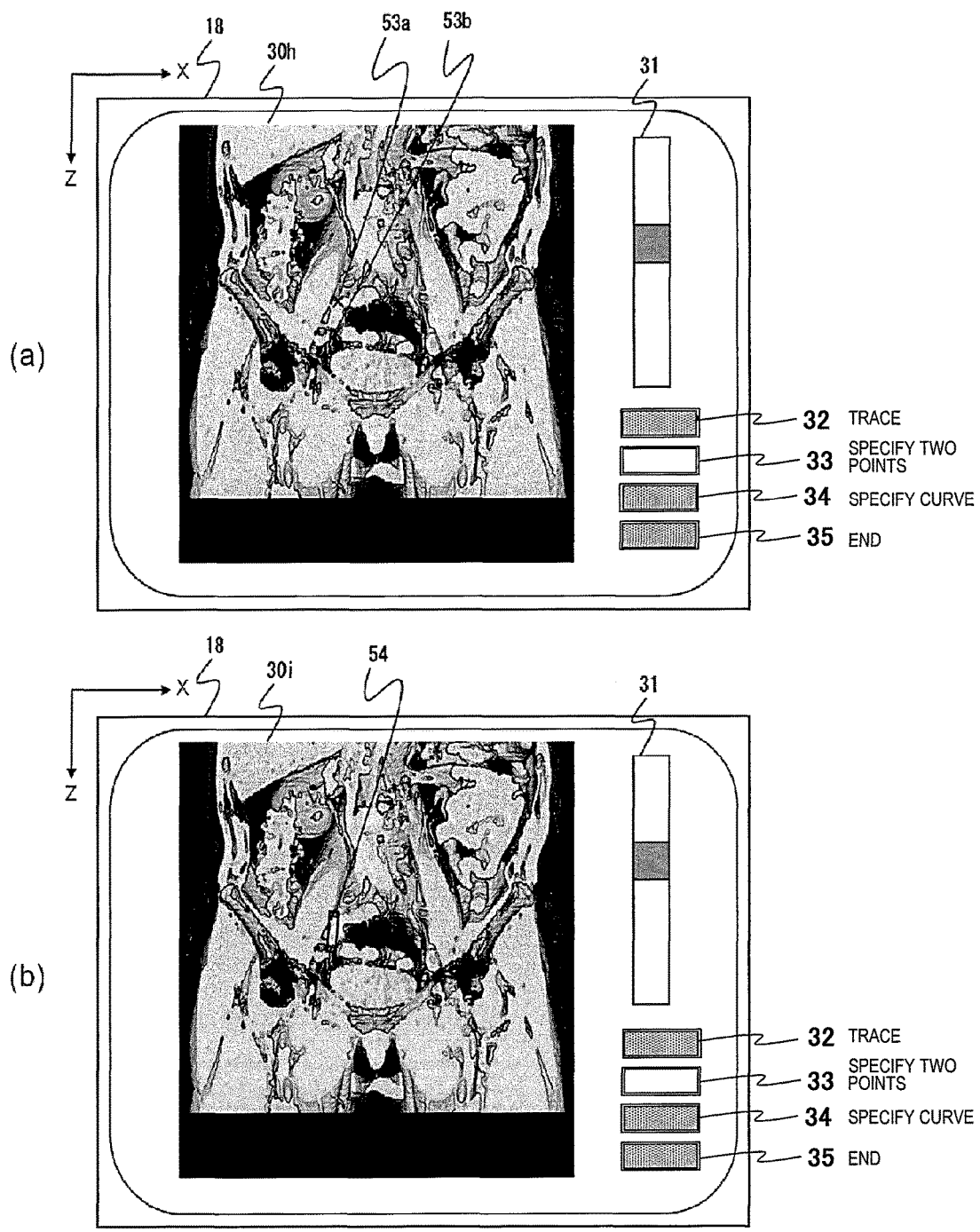
FIG. 13 is a diagram explaining a first variation of an input receiving process of a region of interest.
Figure 14:
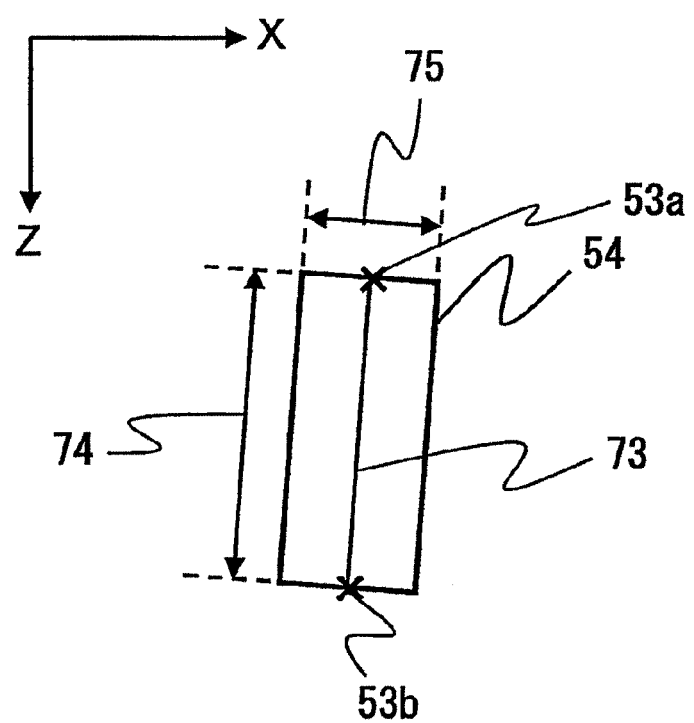
FIG. 14 is a diagram explaining a first variation of an input receiving process of a region of interest.

Referring to FIGS. 13 and 14, the first variation of input reception processing for a region of interest will be described.

In the first variation, two coordinates are specified to receive an input of a region of interest. The calculation unit 2 identifies a position of the region of interest based on the specified two coordinates in addition a position to which the origin of a projection line should move for a pixel in the region of interest.

In the example shown in FIG. 13(a), after an operator presses down the two-point designation button 33 for the first three-dimensional image 30h via the input unit 5 and clicks the mouse pointer 40 twice at a desired position, the coordinate 53a and the coordinate 53b are input.

In the example shown in FIG. 13(a), the urinary tract of the target organ is identified by the coordinate 53a and the coordinate 53b. Between the coordinate 53a and the coordinate 53b, the surrounding organs are located in front of the urinary tract and obscure it. In the first variation, the calculation unit 2 deletes the surrounding organs and constructs a second three-dimensional image where the urinary tract can be observed easily.

The calculation unit 2 sets the square 54 shown in the first three-dimensional image 30i of FIG. 13(b) based on the input coordinate 53a and the coordinate 53b. The square 54 is a region of interest (ROIw). The details for the setting process of the square 54 are shown in FIG. 14.

As shown in FIG. 14, the calculation unit 2 recognizes a length of the line segment 73 that connects the input coordinate 53a and the coordinate 53b as the width 74 in the longitudinal direction of the square 54. Next, the calculation unit 2 specifies a length at a fixed ratio (less than 100%) to the width 74 in the longitudinal direction as the width 75 in the orthogonal direction to the longitudinal direction of the square 54. Then, the calculation unit 2 determines a position of the square 54 so that it is linearly symmetrical with the line segment 73.

Next, the calculation unit 2 refers to depth values of the coordinate 53a and the coordinate 53b, corrects the origin of a projection line for a pixel in the square 54 to a position on the nearer side than the depth values of the coordinate 53a and the coordinate 53b, and then memorizes the position in the storage unit 3.

The calculation unit 2, for example, specifies a correction position of the origin of a projection line to a position on a flat surface where a position in which a constant value (margin) is provided to a depth value of the coordinate 53a on the near side and a position in which a constant value (margin) is provided to a depth value of the coordinate 53b on the near side are connected. In this case, if the depth values of the coordinates 53a and 53b are different each other, a distance from the projection surface to the origin of the projection line for a pixel in the square 54 varies depending on the pixel.

Also, the calculation unit 2, for example, specifies a correction position of the origin of a projection line to a position where a constant value (margin) is provided to a greater depth value between the coordinate 53a and the coordinate 53b on the near side. In this case, distances from all the projection surfaces to the origin of the projection line for a pixel in the square 54 are equal.

Because the origin of a projection line is set to an appropriate position for each projection line by the above processes, the calculation unit 2 can construct a desired image (=image where the urinary tract can be observed easily) by deleting the surrounding organs obscuring the urinary tract.

<Second Variation>

Figure 15:
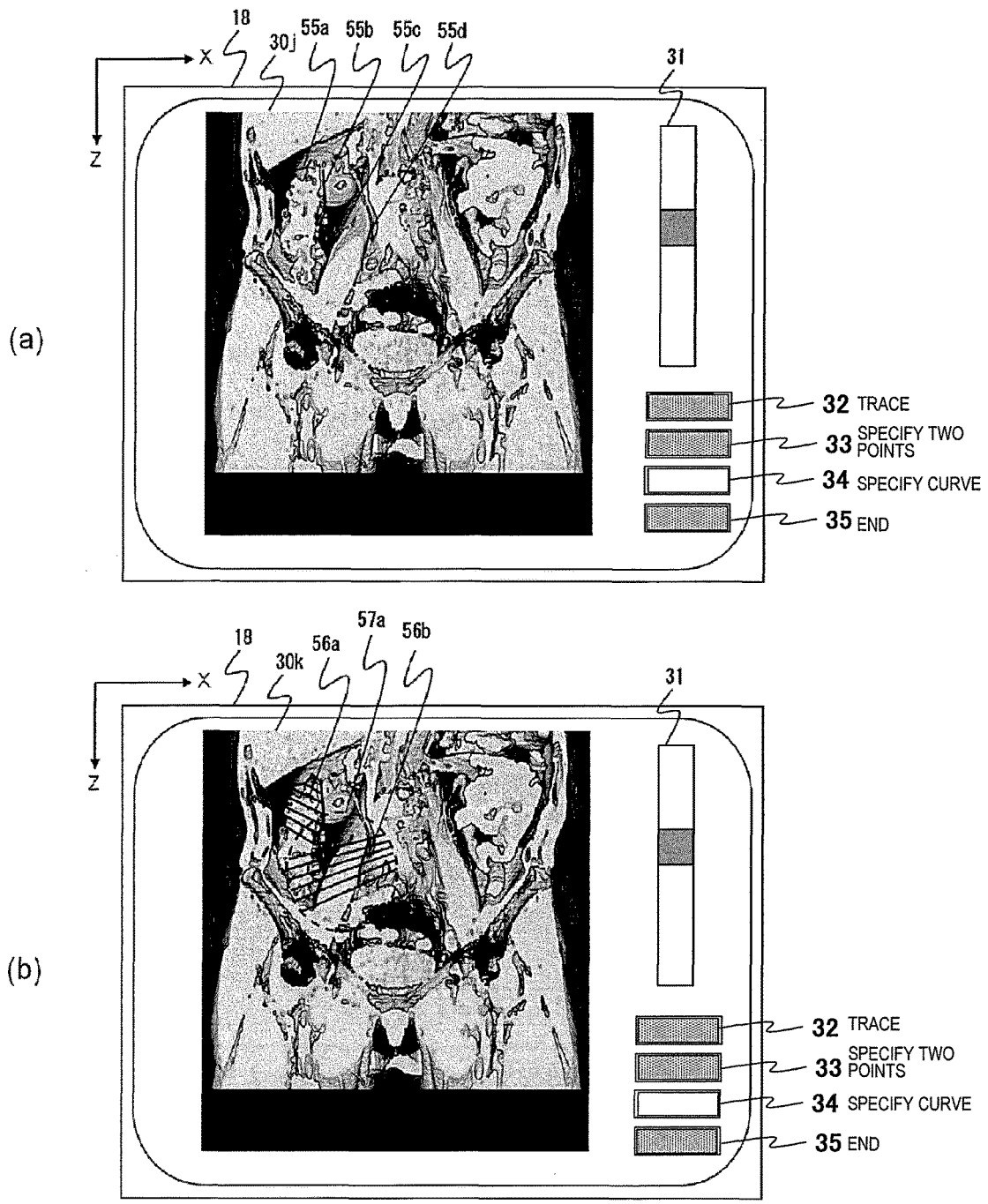
FIG. 15 is a diagram explaining a second variation of an input receiving process of a region of interest.
Figure 16:
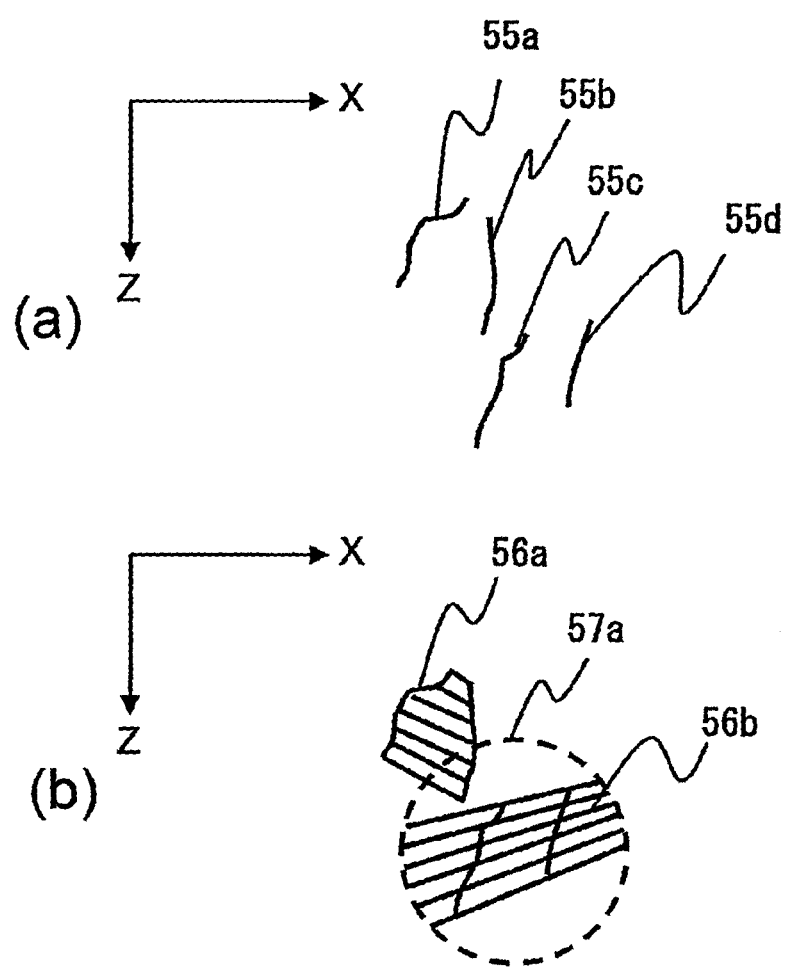
FIG. 16 is a diagram explaining a second variation of an input receiving process of a region of interest.

Referring to FIGS. 15 and 16, the second variation of input reception processing for a region of interest will be described.

In the second variation, two curves are specified to receive an input of a region of interest. The calculation unit 2 identifies a position of the region of interest based on the specified two traces in addition a position to which the origin of a projection line should move for a pixel in the region of interest.

In the example shown in FIG. 15(a), an operator presses down the curve designation button 34 for the first three-dimensional image 30j via the input unit 5 and draws a trace of the mouse pointer 40 four times, the curves 55a, 55b, 55c, and 55d are input. Here, the curves 55a and 55b are a pair of two curves to specify a first region of interest (ROIw1). Similarly, the curves 55c and 55d are a pair of two curves to specify a second region of interest (ROIw2).

In the example shown in FIG. 15(a), the curves 55a and 55b identifies the outer frame of the surrounding organs obscuring the kidney that is a target organ. In the second variation, the calculation unit 2 deletes the surrounding organs and constructs a second three-dimensional image where the kidney can be observed easily.

Also, in the example shown in FIG. 15(a), the curves 55c and 55d identifies the outer frame of the surrounding organs obscuring the urinary tract that is a target organ. In the second variation, the calculation unit 2 deletes the surrounding organs and constructs a second three-dimensional image where the urinary tract can be observed easily.

The calculation unit 2 specifies a region of interest (ROIw) using either of the limit mode limiting a region of interest (ROIw) to a region between two curves or the extension mode extending a region of interest (ROIw) to a circular region that has a constant radius and is centered on the center of gravity of two curves. The limit mode is specified for the oblique line region 56a specified by the curves 55a and 55b.

The extension mode is specified for the oblique line region 56b specified by the curves 55c and 55d.

The calculation unit 2 specifies the oblique line region 56a shown in FIG. 15(b) based on the input curves 55a and 55b. The oblique line region 56a is a first region of interest (ROIw1). The calculation unit 2 specifies a region between the input curves 55a and 55b as the oblique line region 56a in the limit mode.

Also, the calculation unit 2 specifies the oblique line region 56b shown in FIG. 15(b) based on the input curves 55c and 55d. The oblique line region 56b is a second region of interest (ROIw2). The calculation unit 2 specifies a region extended to a circular region that has a constant radius and is centered on the center of gravity of the input curves 55a and 55b as the oblique line region 56b in the extension mode.

Additionally, because FIG. 15(b) is converted into the grayscale image due to the limitations of patent drawings, it is difficult to visually recognize curve traces and oblique line regions. Therefore, FIG. 16 shows only a positional relationship of curve traces and oblique line regions. In fact, because the display unit 4 displays curve traces and oblique line regions in a color different from that of the first three-dimensional image according to the control by the calculation unit 2, an operator can visually recognize curve traces and oblique line regions easily.

Next, the calculation unit 2 refers to depth values on the curve 55a and the curve 55b, corrects the origin of a projection line for a pixel in the square 54 to a position of a depth value on the curve 55a and the curve 55b or a position where a constant value (margin) is provided to a depth value, and then memorizes the position in the storage unit 3. Additionally, a constant value (margin) may be a plus value or a minus value.

The calculation unit 2, for example, specifies a movement position of the origin of a projection line to a position on a curved surface where a position of a depth value on the curve 55a or a position in which a constant value (margin) is provided to the depth value and a position of a depth value on the curve 55b or a position in which a constant value (margin) is provided to the depth value are connected. In this case, if the depth values on the curves 55a and 55b are different each other, a distance from the projection surface to the origin of the projection line for a pixel in the oblique line region 56a varies depending on the projection line.

Similarly, the calculation unit 2, for example, specifies a movement position of the origin of a projection line to a position on a curved surface where a position of a depth value on the curve 55c or a position in which a constant value (margin) is provided to the depth value and a position of a depth value on the curve 55d or a position in which a constant value (margin) is provided to the depth value are connected. In this case, if the depth values on the curves 55c and 55d are different each other, a distance from the projection surface to the origin of the projection line for a pixel in the oblique line region 56b varies depending on the projection line.

Because the origin of a projection line is set to an appropriate position for each projection line by the above processes, the calculation unit 2 deletes the surrounding organs obscuring the kidney and the urinary tract and constructs a desired image (=image where the kidney and the urinary tract can be observed easily).

Additionally, although it is described above that the two curves are to be input, it may also be OK that one closed curve is to be input. This is because the calculation unit 2 can identify the two curves by dividing one closed curve to be input into two. Therefore, when the calculation unit 2 receives an input of a region of interest based on the two curves, an operator may input the two curves or one closed curve.

<Third Variation>

Figure 17:
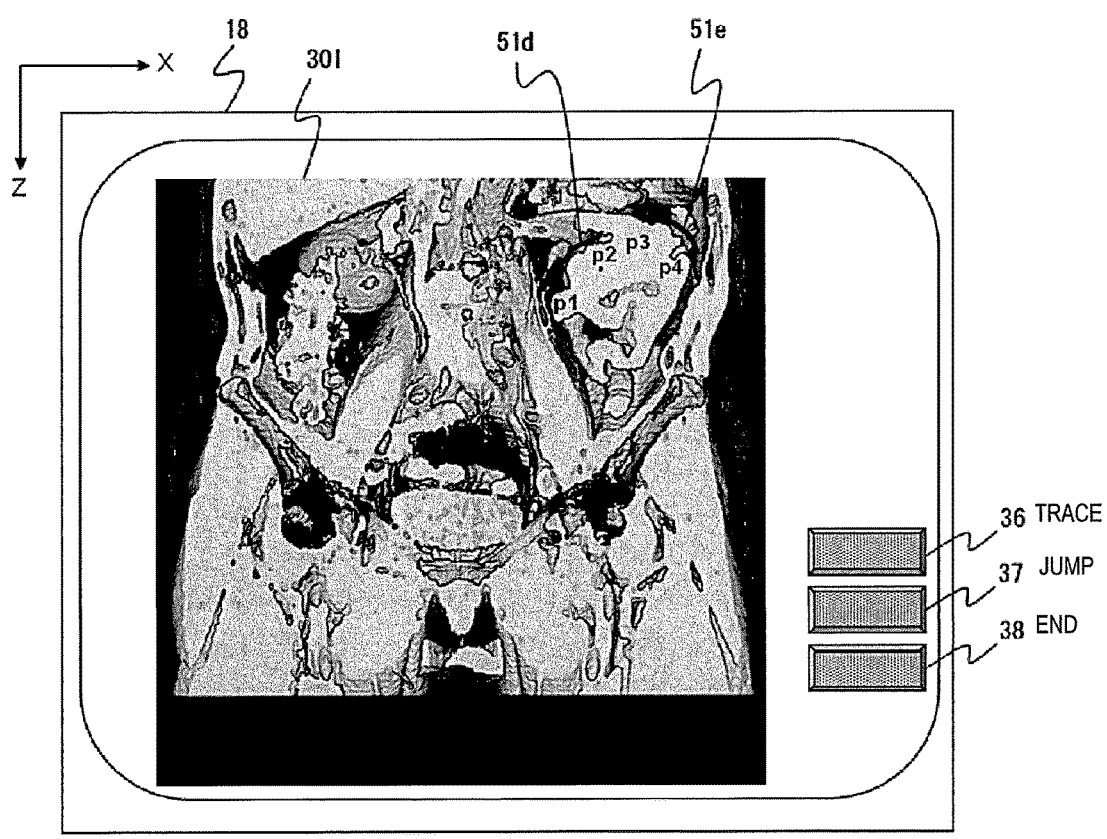
FIG. 17 is a diagram explaining a third variation of an input receiving process of a region of interest.

Referring to FIG. 17, the third variation of input reception processing for a region of interest will be described.

In the third variation, when an operator draws a trace of the mouse pointer 40 via the input unit 5, a trace input can be stopped at a point where depth values are discontinuous.

As shown in the first three-dimensional image 30I in FIG. 17, an operator first presses down the trace button 36 to move the mouse pointer 40 to the coordinate p1 and, for example, drags the mouse pointer 40 to the coordinate p2 while pressing the left click. For this operation, the calculation unit 2 sets the curve 51d where the coordinates p1 and p2 are specified as the starting point and the end point respectively.

Next, an operator presses down the jump button 47 to move the mouse pointer 40 to the coordinate p3 and, for example, drags the mouse pointer 40 to the coordinate p4 while pressing the left click. For this operation, the calculation unit 2 sets the curve 51e where the coordinates p3 and p4 are specified as the starting point and the end point respectively.

The calculation unit 2 refers to a depth value of the corresponding depth image for points on the curves 51d and 51e to perform correction processing for the origin of a projection line. On the other hand, the calculation unit 2 refers to a value interpolated by depth values of the coordinates p2 and p3 for points between the coordinates p2 and p3 to perform correction processing for the origin of a projection line.

Because an operator can order not to refer to depth values of the surrounding organs to be deleted when the third variation is applied to the second variation, the calculation unit 2 can set the origin of a projection line to an appropriate position for each projection line. Additionally, the calculation unit 2 can delete the surrounding organs obscuring the kidney and construct a desired image (=image where the kidney can be observed easily).

Second Embodiment

Figure 18:
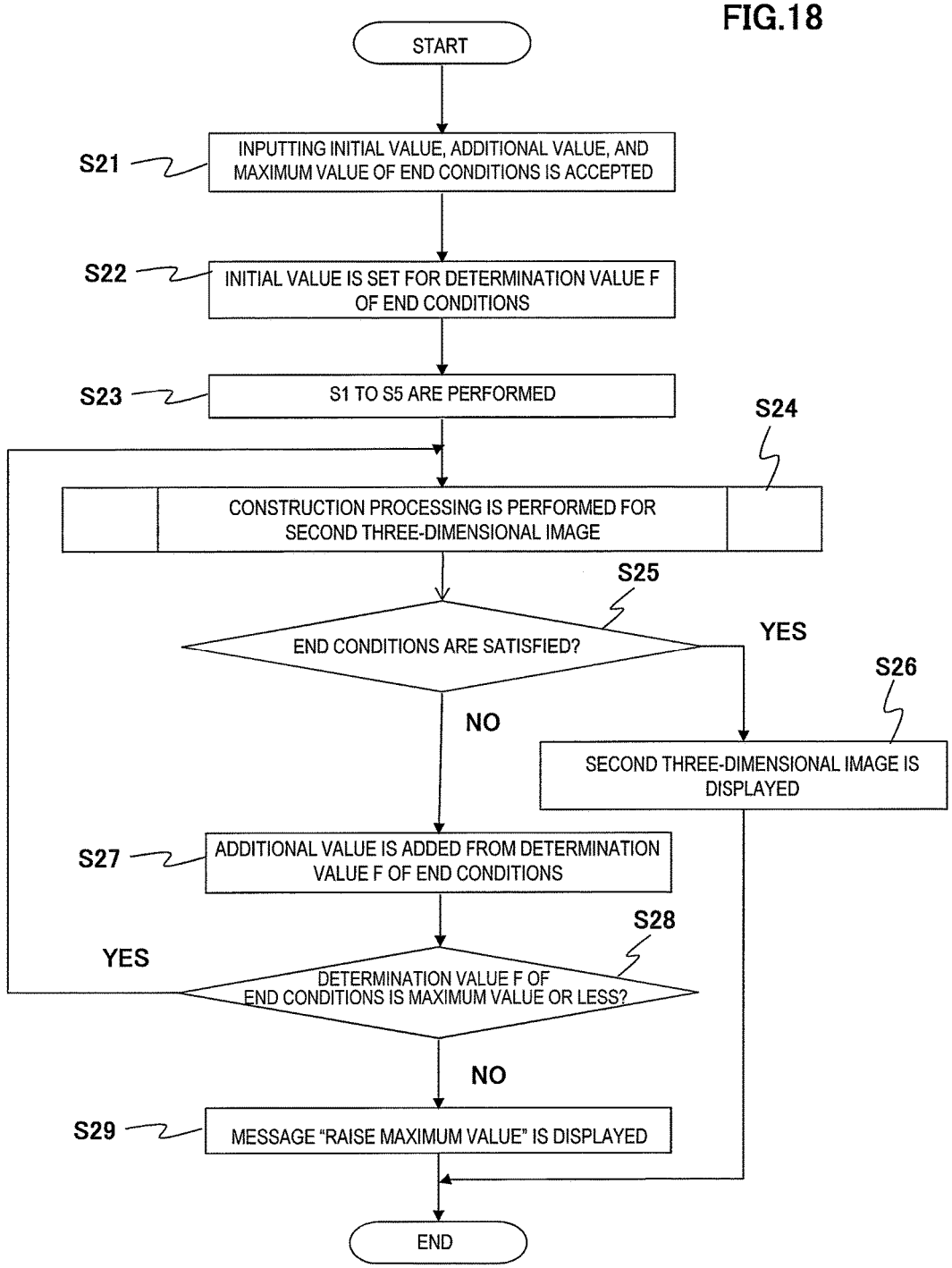
FIG. 18 is a flow chart showing the entire process flow in the second embodiment.
Figure 19:
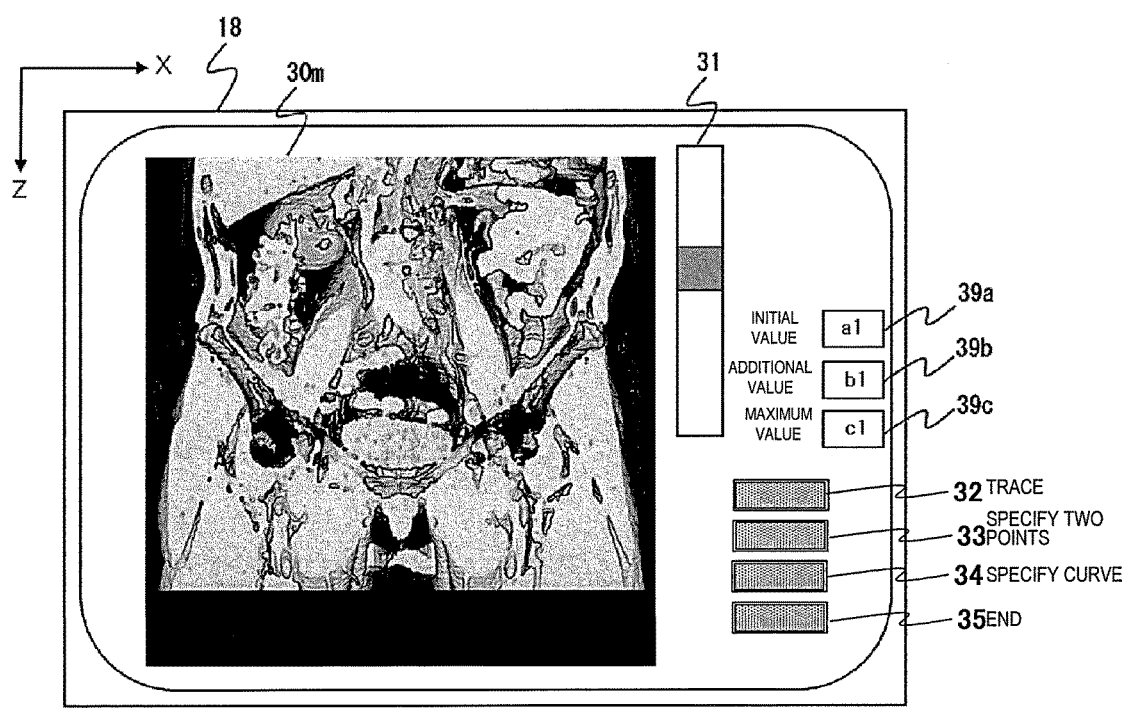
FIG. 19 is a diagram explaining an input receiving process of a termination condition parameter.

Referring to FIGS. 18 and 19, the second embodiment will be described. In the second embodiment, a case where a second three-dimensional image is not constructed in the first embodiment can be avoided as possible. Therefore, in the second embodiment, if the origin of a projection line is moved to a limit position (Yes for S14) at S14 in FIG. 3, the calculation unit 2 repeats construction processing for a second three-dimensional image after changing end conditions.

As shown in FIG. 18, the calculation unit 2 receives inputs of an initial value, addition value, and maximum value of the end conditions in construction processing for a second three-dimensional image via the input unit 5 (S21).

In FIG. 19, it is shown that the initial value input box 39a, the addition value input box 39b, and the maximum value input box 39c are displayed with the first three-dimensional image 30m on the display 18.

An operator inputs desired initial, addition, and maximum values for each of the initial value input box 39a, the addition value input box 39b, and the maximum value input box 39c via the input unit 5. The calculation unit 2 executes the subsequent processes using input values for each of the initial value input box 39a, the addition value input box 39b, and the maximum value input box 39c.

Going back to the description of FIG. 18, next, the calculation unit 2 sets an initial value input at S21 for the determination value F of the end conditions (S22), performs S1 to S5 of FIG. 2 (S23), and then executes construction processing for the second three-dimensional image shown in FIG. 3 (S24). Here, the determination value F of the end conditions is the determination value D or E in the first embodiment.

Next, the calculation unit 2 checks whether the end conditions are satisfied or not in construction processing for the second three-dimensional image (S25). Because the second three-dimensional image has been constructed in a case where the end conditions are satisfied (Yes for S25), the calculation unit 2 displays the second three-dimensional image (S26).

In a case where the end conditions are not satisfied (No for S25), the calculation unit 2 adds an addition value input at S21 to the determination value F of the end conditions (S27).

Next, the calculation unit 2 checks whether the determination value F of the end conditions is equal to or less than a maximum value input at S21 or not (S28). In a case where the determination value F of the end conditions is equal to or less than a maximum value (Yes for S28), the calculation unit 2 repeats processes from S24. In a case where the determination value F of the end conditions is greater than a maximum value (No for S28), the display unit 4 displays the message "Increase the maximum value." according to the control by the calculation unit 2 (S29). In this case, processes are to be repeated from S21.

As described above, according to the second embodiment, a case where a second three-dimensional image is not constructed in the first embodiment can be avoided as possible.

Third Embodiment

Referring to FIGS. 20 to 23, the third embodiment will be described. The third embodiment shows the details of correction processing for the origin of a projection line. The third embodiment is effective in a case where surrounding organs to be deleted becomes larger as being away from the origin surface in the process of correcting the origin of the projection line. In the second embodiment, the calculation unit 2 radially scans a pixel of the circle 84 of a certain radius R with the point P on the origin line 83 centered.

Figure 20:
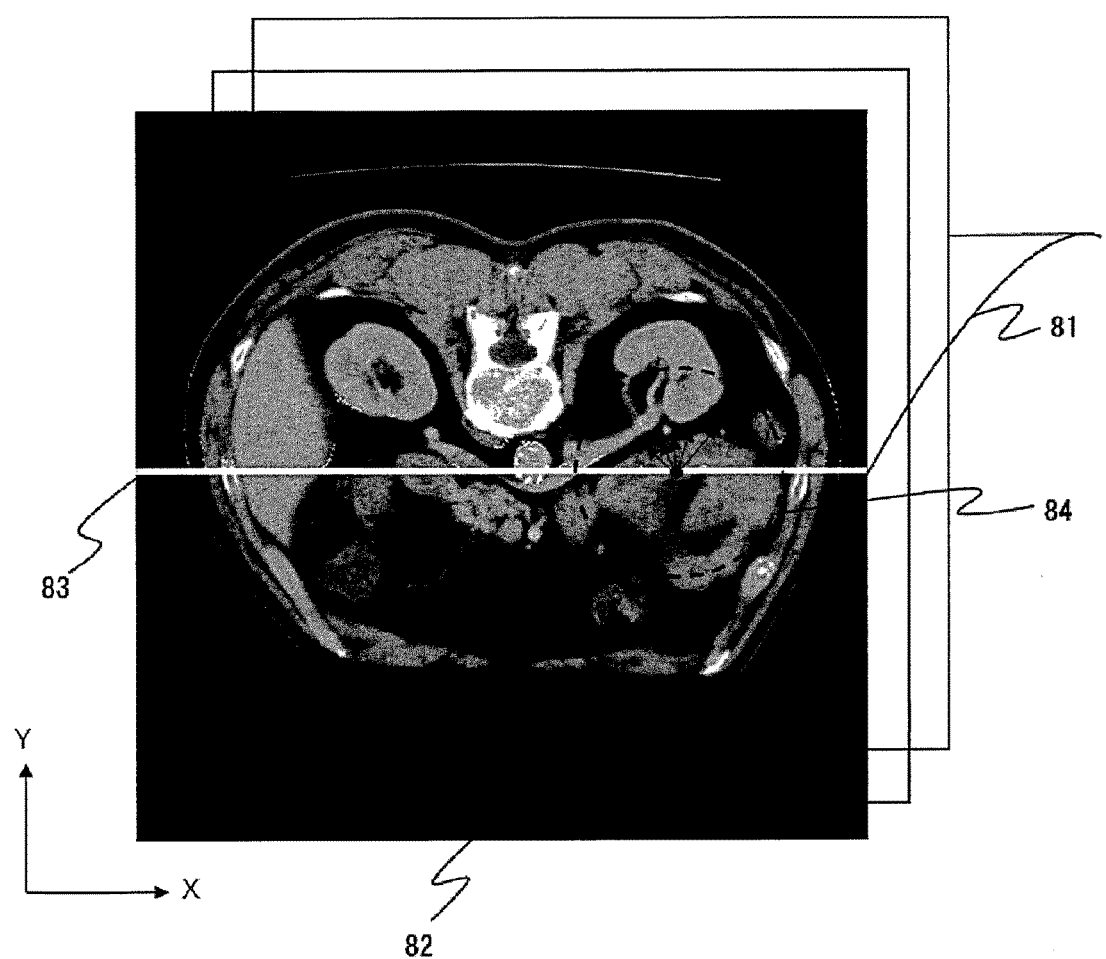
FIG. 20 is a diagram explaining a process of constructing a three-dimensional image in the third embodiment.

Hereinafter, processes of the calculation unit 2 are considered for each axial surface. As shown in FIG. 20, the intersection line (white thick line) of the origin surface 81 and the axial surface 82 is the origin line 83 to be a processing target on the axial surface 82. The calculation unit 2 executes correction processing of the origin of a projection line for the point P satisfying threshold conditions located on the origin line 83. Here, the threshold conditions are those with a degree where organs can be distinguished from the air and are to satisfy the threshold conditions at a pixel value belonging to the organs.

Figure 21:
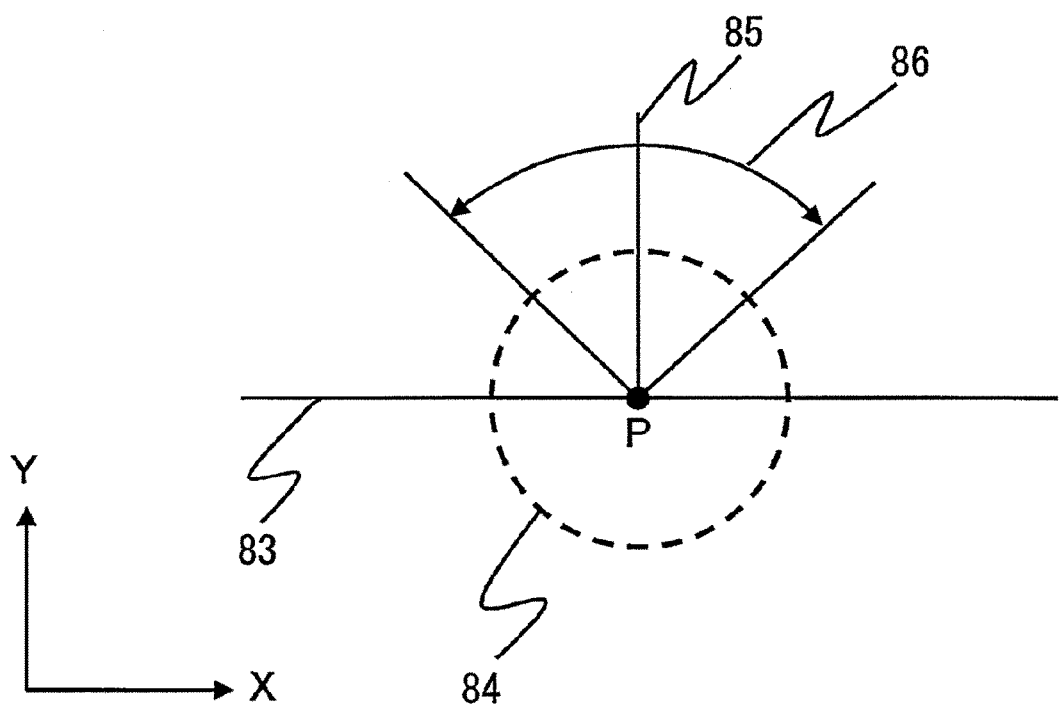
FIG. 21 is a diagram explaining a process of constructing a three-dimensional image in the third embodiment.

Specifically, as shown in FIG. 21, the calculation unit 2 centers the reference line 85 running through the point P and orthogonal to the origin line 83 to radially scan a pixel in a direction within the certain angle range 86. Then, if there is a pixel (=a pixel does not belong to organs) that does not satisfy the above threshold conditions, the calculation unit 2 specifies the position as the origin of a projection line. The calculation unit 2 can set the origin of a projection line between a surrounding organ to be deleted and the target organ by executing this process for all the points P satisfying the threshold conditions located on the origin line 83.

FIG. 22 shows a case where the calculation unit 2 scans a pixel only in a direction orthogonal to the origin line 83.

In an example of FIG. 22(a), the aim is to set the origin of a projection line between the target organ 91 and the surrounding organ 92.

The thick line 87 is the intersection line of a region of interest set by an operator and the axial surface. Because an operator traces the circumference of a region of the surrounding organ 92 to be deleted while visually checking only a first three-dimensional image being displayed on the display unit 4, the region of interest is located as shown in FIG. 22(a). The calculation unit 2 scans a pixel in a direction orthogonal to the origin line 83 for each point on the thick line 87 from the point P1 to the point P2 to correct the origin of a projection line.

FIG. 22(b) shows a result of correcting the origin of a projection line. The origin of the projection line is corrected in the region of interest and is located at the thick line 89b. On the other hand, because the origin of the projection line is not corrected on the outside of the region of interest, the origin of the projection line remains at an initial value as it was and is located at the thick lines 89a and 89c. In this state, the target organ 91 remains obscured by the surrounding organ 92 at the positions of the thick lines 89a and 89c.

On the other hand, FIG. 23 shows a case where the calculation unit 2 radially scans a pixel of the circle 84 with a certain radius R in which the point P on the origin line 83 is centered. Similarly to the example of FIG. 22(a), also in an example of FIG. 23(a), the aim is to set the origin of a projection line between the target organ 91 and the surrounding organ 92.

Similarly to FIG. 22(a), the thick line 87 is the intersection line of a region of interest set by an operator and the axial surface. The calculation unit 2 radially scans a pixel of the circle 84 with a certain radius R in which each point on the thick line 87 from the point P1 to the point P2 is centered to correct the origin of a projection line.

FIG. 23(b) shows a result of correcting the origin of a projection line. The result of correcting the origin of the projection line based on points in the region of interest is the position of the thick line 89e. The other results are the positions of the thick lines 89d and 89f. In this case, the target organ 91 can be observed without obscuring the surrounding organ.

As described above, although the suitable embodiments of a three-dimensional image construction apparatus etc. related to the present invention are described while referring to the attached diagrams, the present invention is not limited to such examples. It is obvious that a person skilled in the art can devise various alterations or modifications within the scope of the technical ideas disclosed in the present invention, and it is to be understood that these alterations and modifications belong, as a matter of course, to the technical scope of the present invention.

DESCRIPTION OF REFERENCE NUMERALS

1: three-dimensional image construction apparatus, 2: calculation unit, 3: storage unit, 4: display unit, 5: input unit

The invention claimed is:

1. A three-dimensional image construction apparatus comprising:
   a display unit displaying a first three-dimensional image on a predetermined origin surface;
   an input unit receiving an input of a region of interest for a second three-dimensional image, in the first three-dimensional image; and
   a calculation unit setting the origin surface as an initial value of the origin of a projection line to construct the second three-dimensional image, correcting the origin of the projection line for a pixel in the region of interest based on a depth image corresponding to the first three-dimensional image, and then constructing the second three-dimensional image using the corrected origin of the projection line for the region of the interest;
   wherein the calculation unit:
      extracts a first image region based on a depth gradient of the depth image in the region of interest,
      corrects the origin of the projection line for the pixel in the first image region to a direction opposite to a projection direction or the projection direction by a certain distance as the first step of repetitive processing and memorizes the corrected origin of the projection line in a storage unit,
      extracts a second image region based on a depth gradient of the depth image on the basis of the corrected origin of the projection line as the second step of repetitive processing in the first image region,
      determines whether the second image region satisfies end conditions or not as the third step of repetitive processing,
      sets the second image region as the new first image region if the end conditions are not satisfied and repeats the third step from the first step until the end conditions are satisfied, and then
      constructs the second three-dimensional image using the corrected origin of the projection line memorized in the storage unit for the region of the interest if the end conditions are satisfied.

2. The three-dimensional image construction apparatus according to claim 1,
   wherein the end conditions are based on areas of the first image region and the second image region.

3. The three-dimensional image construction apparatus according to claim 1,
   wherein the end conditions are based on only an area of the second image region.

4. The three-dimensional image construction apparatus according to claim 1,
   wherein the calculation unit changes a determination value of the end conditions in a case where the corrected origin of the projection line exceeds a limit position.

5. The three-dimensional image construction apparatus according to claim 1,
   wherein the input unit receives an input of two coordinates in the first three-dimensional image to be displayed on the display, and
   the calculation unit determines the region of interest based on positions of the two coordinates and corrects the origin of the projection line for a pixel of the region of interest based on a pixel value of the depth image at the two coordinates.

6. The three-dimensional image construction apparatus according to claim 1,
   wherein the input unit receives an input of two curves in the first three-dimensional image to be displayed on the display, and
   the calculation unit determines the region of interest based on positions of the two curves and corrects the origin of the projection line for a pixel of the region of interest based on a pixel value of the depth image on the two curves.

7. The three-dimensional image construction apparatus according to claim 6, wherein the calculation unit determines the region of interest by using either of a limit mode where the region of interest is limited to a region between the two curves or an extension mode where the region of interest is extended to the outside of a region between the two curves.

8. The three-dimensional image construction apparatus according to claim 6,
wherein the input unit receives an interruption and resume of a trace input while receiving the trace input of the curves, and
the calculation unit interpolates a pixel value of the depth image for a pixel between an interrupted position and a resume position of the trace input by using a pixel value of the depth image in the interrupted position and a pixel value of the depth image in the resume position.

9. The three-dimensional image construction apparatus according to claim 1,
wherein the calculation unit corrects the origin of the projection line for a pixel in the region of interest by performing threshold processing radially in a certain angle range with a projection direction centered from a pixel in the region of interest.

10. The three-dimensional image construction apparatus according to claim 1,
wherein the display unit displays a position of the corrected origin of the projection line with it superimposed on a tomographic image.

11. The three-dimensional image construction apparatus according to claim 1,
wherein the display unit displays a depth position of the depth image with it superimposed on a tomographic image.

12. A three-dimensional image construction method executing:
displaying, via a display unit, a first three-dimensional image on a predetermined origin surface;
receiving, via an input unit, an input of a region of interest for a second three-dimensional image, in the first three-dimensional image;
setting, via a calculation unit, the origin surface as an initial value of the origin of a projection line to construct a second three-dimensional image;
correcting, via the calculation unit, the origin of the projection line for a pixel in the region of interest based on a depth image corresponding to the first three-dimensional image; and
constructing, via the calculation unit, the second three-dimensional image using the corrected origin of the projection line for the region of interest;
wherein the calculation unit:
extracts a first image region based on a depth gradient of the depth image in the region of interest,
corrects the origin of the projection line for the pixel in the first image region to a direction opposite to a projection direction or the projection direction by a certain distance as the first step of repetitive processing and memorizes the corrected origin of the projection line in a storage unit,
extracts a second image region based on a depth gradient of the depth image on the basis of the corrected origin of the projection line as the second step of repetitive processing in the first image region,
determines whether the second image region satisfies end conditions or not as the third step of repetitive processing,
sets the second image region as the new first image region if the end conditions are not satisfied and repeats the third step from the first step until the end conditions are satisfied, and then
constructs the second three-dimensional image using the corrected origin of the projection line memorized in the storage unit for the region of the interest if the end conditions are satisfied.

* * * * *